(12) United States Patent
Lynn et al.

(10) Patent No.: US 7,081,095 B2
(45) Date of Patent: Jul. 25, 2006

(54) CENTRALIZED HOSPITAL MONITORING SYSTEM FOR AUTOMATICALLY DETECTING UPPER AIRWAY INSTABILITY AND FOR PREVENTING AND ABORTING ADVERSE DRUG REACTIONS

(76) Inventors: Lawrence A. Lynn, 1507 Chambers Rd., Columbus, OH (US) 43212; Eric N. Lynn, 4901 Walnut Grove, Villa Ridge, MO (US) 63089

( * ) Notice: Subject to any disclaimer, the term of this patent is extended or adjusted under 35 U.S.C. 154(b) by 278 days.

(21) Appl. No.: 10/150,582

(22) Filed: May 17, 2002

(65) Prior Publication Data

US 2003/0000522 A1   Jan. 2, 2003

Related U.S. Application Data

(60) Provisional application No. 60/291,691, filed on May 17, 2001, provisional application No. 60/291,687, filed on May 17, 2001, provisional application No. 60/295,484, filed on Jun. 1, 2001.

(51) Int. Cl.
*A61B 5/00* (2006.01)
(52) U.S. Cl. .................. 600/538; 600/300; 128/203.23
(58) Field of Classification Search ..................... None
See application file for complete search history.

(56) References Cited

U.S. PATENT DOCUMENTS

| | | | |
|---|---|---|---|
| 4,106,503 A | 8/1978 | Rosenthal et al. | |
| 4,365,636 A | 12/1982 | Barker | |
| 4,523,279 A | 6/1985 | Sperinde | |
| 4,630,614 A | 12/1986 | Atlas | |
| 4,651,746 A | 3/1987 | Wall | |
| 4,738,266 A | 4/1988 | Thatcher | |
| 4,757,824 A | 7/1988 | Chaumet | |
| 4,765,340 A | 8/1988 | Sakai | |
| 4,802,485 A | 2/1989 | Bowers | |
| 4,869,253 A | 9/1989 | Craig | |
| 5,199,424 A | 4/1993 | Sullivan | |
| 5,206,807 A | 4/1993 | Hatke | |
| 5,233,983 A | 8/1993 | Markowitz | |
| 5,275,159 A | 1/1994 | Griebel | |

(Continued)

FOREIGN PATENT DOCUMENTS

DE   9 200 422   7/1992

(Continued)

OTHER PUBLICATIONS

Alaris System, Brochure, Medication Safety System Focused at the Point of Care, Cardinal Health, Alaris Products, pp. 8.

(Continued)

*Primary Examiner*—Robert L. Nasser
(74) *Attorney, Agent, or Firm*—Fletcher Yoder

(57) ABSTRACT

A system and method for the automatic diagnosis of obstructive sleep apnea in a centralized hospital critical care monitoring system for the monitoring of a plurality of patients in at least one of a critical care, step down, and cardiac ward by telemetry. The system includes a central processor having a display, and a plurality of telemetry units for mounting with patients, each of the telemetry units has a plurality of sensors for connection with each patient, the telemetry unit is capable of the transmission of multiple signals derived from the sensors to the central processor, in one preferred embodiment the method comprising steps of programming the system to analyze the signals and to automatically identify the presence and severity of obstructive sleep apnea and to provide an indication of the identification.

7 Claims, 29 Drawing Sheets

U.S. PATENT DOCUMENTS

| | | | |
|---|---|---|---|
| 5,318,597 A | 6/1994 | Hauck et al. | |
| 5,335,654 A | 8/1994 | Rapoport | |
| 5,353,788 A | 10/1994 | Miles | |
| 5,368,026 A | 11/1994 | Swedlow | |
| 5,385,144 A | 1/1995 | Yamanishi | |
| 5,398,682 A | 3/1995 | Lynn | |
| 5,483,969 A | 1/1996 | Testerrman | |
| 5,485,851 A | 1/1996 | Erickson | |
| 5,540,733 A | 7/1996 | Testerman | |
| 5,605,151 A | 2/1997 | Lynn | |
| 5,645,053 A | 7/1997 | Remmers | |
| 5,645,054 A | 7/1997 | Cotner | |
| 5,682,878 A * | 11/1997 | Ogden | 128/204.23 |
| 5,704,345 A | 1/1998 | Berthon-Jones | |
| 5,740,795 A | 4/1998 | Brydon | |
| 5,743,250 A | 4/1998 | Gonda et al. | |
| 5,765,563 A | 6/1998 | VanderSchaaf | |
| 5,769,084 A | 6/1998 | Katz | |
| 5,794,615 A * | 8/1998 | Estes | 128/204.23 |
| 5,803,066 A | 9/1998 | Rapoport | |
| 5,827,179 A | 10/1998 | Lichter | |
| 5,830,135 A | 11/1998 | Bosque | |
| 5,865,736 A | 2/1999 | Baker | |
| 5,891,023 A | 4/1999 | Lynn | |
| 5,902,250 A | 5/1999 | Verrier | |
| 5,957,885 A | 9/1999 | Bollish | |
| 6,006,379 A | 12/1999 | Hensley | |
| 6,015,388 A | 1/2000 | Sackner | |
| 6,083,156 A | 7/2000 | Lisiecki | |
| 6,105,575 A * | 8/2000 | Estes et al. | 128/204.23 |
| 6,120,441 A | 9/2000 | Griebel | |
| 6,148,814 A | 11/2000 | Clemmer et al. | |
| 6,223,064 B1 | 4/2001 | Lynn et al. | |
| 6,342,039 B1* | 1/2002 | Lynn et al. | 600/529 |
| 6,425,861 B1* | 7/2002 | Haberland et al. | 600/300 |
| 6,463,326 B1 | 10/2002 | Hartley et al. | |
| 6,519,486 B1 | 2/2003 | Edgar, Jr. et al. | |
| 6,529,752 B1 | 3/2003 | Krausman et al. | |
| 6,609,016 B1 | 8/2003 | Lynn | |
| 6,637,434 B1 | 10/2003 | Noble | |
| 6,691,705 B1 | 2/2004 | Dittman et al. | |
| 6,745,764 B1 | 6/2004 | Hickle | |
| 6,760,608 B1 | 7/2004 | Lynn | |
| 6,807,965 B1 | 10/2004 | Hickle | |
| 6,832,200 B1 | 12/2004 | Greevan et al. | |
| 2002/0162558 A1* | 11/2002 | Noble | 128/207.18 |
| 2004/0170154 A1* | 9/2004 | Carter et al. | 370/338 |
| 2005/0027207 A1* | 2/2005 | Westbrook et al. | 600/529 |

FOREIGN PATENT DOCUMENTS

| | | |
|---|---|---|
| WO | WO 8 801 149 | 2/1988 |
| WO | WO 9 009 146 | 8/1990 |

OTHER PUBLICATIONS

Agilent Technologies, Agilent M1165/66/67/75/76/77A Component Monitoring System and Agilent M1205A V24 & V26, User's Reference Manual, vol. 1, System Information, Part No. M1046-9101L, First Ed., Printed Nov. 2000 (See, e.g., Chapter 9, pp. 9-2, 9-3, 9-6, 9-10 and 9-19).

Agilent Technologies, Agilent M1165/66/67/75/76/77A Component Monitoring System and Agilent M1205A V24 & V26, User's Reference Manual, vol. 2, Parameter Information, Part No. M1046-9101L, First Ed., Printed Nov. 2000.

Aubry, et al., The $SaO_2/t$ Diagram as A Useful Means To Express Nocturnal Hypoxemia, Chest, 1989; 96: 1341-45.

Bartolo, Anton, et al., An Arrhythmia Detector and Heart Rate Estimator For Overnight Polysomnography Studies, conditionally accepted for IEEE Transactions, 19 pages.

Blackshear et al., Nocturnal Dyspnea And Atrial Fibrillation Preset Cheyne—Stokes Respirations In Patients With Congestive Heart Failure, Jun. 26, 1995, Arch Intern Med. vol. 155, p. 1296-1302.

Buckle, Patricia, et al., Polysomnography in Acutely Ill Intensive Care Unit Patients, Chest, v. 102 n. 1, p. 288 (4), American College of Chest Physicians.

Dowdell, WT; Javaheri, S; McGinnis, W, Cheyne-Stokes Respiration Presenting as Sleep Apnea Syndrome. Clinical Polysomnographic Features, Am Rev Respir Dis, Apr. 1990, pp. 871-879.

Dyken, Mark Eric et al., Obstructive Sleep Apnea Associated with Cerebral Hypoxemia and Death, Neurology 2004; 62, pp. 491-493.

Epstein et al., "Cost-Effectiveness Analysis Of Nocturnal Oximetry As A Method Of Screening For Sleep Apnea-Hypopnea Syndrome," Jan. 1, 1998, Chest, vol. 113, p. 97-103.

Evans, et al., A Microcomputer System for Monitoring and Analysing Oxyhemolobin Saturation During Sleep. Computer Programs in Biomedicine, 1984; 18:227-234.

Fletcher et al., Effect of Cardiac Output Reduction on Rate of Desaturation in Obstructive Apnea; Chest, 99:452-456, 1991.

Fletcher et al., Rate of Oxyhemolglobin Desaturation in Obstructive versus Nonobstructive Apnea; Am Rev Respi Dis. 143:657-660; 1990.

Fletcher et al., The Rate of Fall of Arterial Oxyhemoglobin Saturation in Obstructive Sleep Apnea, Chest, 1989; 96: 717-722.

Gagnadoux, Fredrick et al., *Home Unattended* vs *Hospital Telemonitored Polysomnography in Suspected Obstructive Sleep Apnea Syndrome*: A Randomized Crossover Trial, Chest 2002; 121; 753-758.

Gami, Apoor S. et al., Day-Night Pattern of Sudden Death in Obstructive Sleep Apnea, The New England Journal of Medicine, 2005; 352, pp. 1206-1214.

George et al., Identification on Qualification of Apneas by Computer-based Analysis of Oxygen Saturation, American Review of Respiratory Disease, 1988; 137; 1238-1240.

Griffiths, et al., A Video System for Investigating Breathing Disorders During Sleep, Thorad, 1991; 46: 136-140.

Guilleminault et al., Sleep Apnea Syndrome: Can It Induce Hemodynamic Changes?, Western Journal of Medicine, vol. 123, Jul. 1975, pp. 7-16.

Guilleminault, C. et al., Unattended CPAP Titration: Toward A Smart Machine, May 20, Stanford University Sleep Research Center, 1 page.

Gyulay et al., A Comparison of Clinical Assessment and Home Oximetry in the Diagnosis of Obstructive Sleep Apnea, American Review of Respiratory Disease, 1993; 147: 50-53.

Hoch, et al., Uberprufung der Fruherkennungsmethode MESAM und Biox 3700 zur Erfassung Schlafbezogener Atmmgmsergulationsstorungen bei jungen Mannern, Pneumologie, 1991; 45: 217-222 (and translation).

Hoffarth, et al., Beuteilung Pulsoximetrisch Erfasster zklisheer.. and translation (Hoffarth et al. Assessment of Cyclic and Phasic Oxygen Desaturations Measured via Pulsoximetry in Nocturnal Diagnosis of Respiratory Regulation Disorders, Peumologie, May 1991; 45: 229-232.

Jain, Sanjay S., et al., Perioperative Treatment of Patients with Obstructive Sleep Apnea, Current Opinion Pulmonary Medicine 10, pp. 482-488, 2004.

Keyl, C., et al., Spektralanalyse von Arterieller Sauerstoff-sättigung und RR-Intervallen bei Patienten mit obstrukitver Schlafapnoe, Wein Med Wschr 1995, pp. 515-516 (vol. 145).

Kirby et al., Computer Quantitation of Sturation Impairment Time As An Index of Oxygenation During Sleep, Com Meth, 1992: 107-115.

Koehler, U., et al., Nocturnal Myocardial Ischemia and Cardiac Arrhythmia in Patients with Sleep Apnea with and Without Coronary Heart Disease (1991) 69; 474-482.

Longobardo et al., Sleep Apnea Considered As A Control System Instability, Sep. 1982, Respiratory Physiology 50: 311-333.

Lynn, Lawrence A., Cluster Analysis: A New Technology for the Evaluation of Oximetry and Airflow Waveforms in Obstructive Sleep Apnea, Accepted after revision on Dec. 20, 1997, 17 total pages.

Pae, Eung-Kwon, et al., Neuroscience Letters 375, 2005, pp. 123-128.

Pepin et al., Does Oximetry contribute to the Detection of Apneic Events? Mathematical. Processing of the $SaO_2$ Signal, Chest, May 1991; 99: 1151-1157.

Rapoport, et al., CO2 Homeostasis During Periodic Breathing: Predictions From A Computer Model, The American Journal of Applied Physiological, 1993, vol. 75, Issue 5, pp. 2302-2309.

Rauscher et al., Computerized Detection of Respiratory Events During Sleep from Rapid Increases in Oxyhemoglobin Saturation, Lung, 1991; 169: 355-42.

Rauscher et al., Quantification of sleep-disordered breathing by computerized analysis of oximetry, heart rate, and snoring, Eur Respir J. Jun. 1991; 4: 655-659.

Ryan, Clodagh M., et al., Periodicity of Obstructive Sleep Apnea in Patients With and Without Heart Failure, Chest 2005; 127, pp. 536-542.

Salmi, et al., Evaluation of Automatic Analysis of SCSB, Airflow and Oxygen Saturation Signals in Patients with Sleep Related Apneas, Chest, 1989; 96: 255-61.

Sanders et al., Obstructive Sleep Apnea Teated by Independently Adjusted Inspiratory and Expiratory Positive Airway Pressures via Nasal Mask, Chest, 1990: 98: 317-24.

Scharf, Steven M., et al., Cardiovascular Effects of Periodic Occlusions of the Upper Airways in Dogs, American Review of Respiratory Disease, pp. 321-329.

Series, et al., Influence of Continuous Positive Airways Pressure on Sleep Apnea-Related Desaturation in Sleep Apnea Patients, Lung, 1992; 170: 281-290.

Series et al., "Utility of Nocturnal Home Oximetry for Case Finding in Patients with Suspected Sleep apnea Hypopnea Syndrome," Sep. 15, 1993, Annals of Internal Medicine, col. 119, p. 449-453.*

Shepard, J., Gas Exchange and Hemodynamics During Sleep, Medical Clinics of North America, vol. 69, No. 6, Nov. 1985, pp. 1243-1265.

Slutsky et al., Quantification of Oxygen Saturation During Episodic Hypoxemia, American Review of Respiratory Disease, 1980; 121:893-895.

Staniforth, Ad; Kinnear, WJ; Starling, R; Cowley Aj, Nocturnal desaturation in Patients with Stable Heart Failure, Heart, Apr. 1998; pp. 394-399.

Strohl et al., Oxygen Saturation During Breath Holding and During Apneas in Sleep, Chest, Feb. 1984: 85, No. 1; 181-186.

Svanborg, et al., A Limited Diagnostic Investigation for Obstructive Sleep Apnea Syndrome: Oximetry and Static Charge Sensitive Bed, Chest, 1990; 98: 1341-45.

Tan and T. H. Koh, Evaluation of Obstructive Sleep Apnea in Singapore Using Computerized Polygraphic Monitoring, Annals Academy of Medicine, Mar. 1991, vol. 20 No. 2, pp. 196-200.

Timms et al., Oxygen Saturation by Oximetry: analysis By Microcomputer, Journal of Polysomographic Technology, Spring 1988: 13-21.

Timms, et al., and Profox Associates, Inc., Profox for the Bedside, Version 8SP Nov. 1992, Programs for Oximetry [IBM], User's Manual, Nov. 1992, 20 total pages.

White, D. P., et al., Assessment of Accuracy and Analysis Time of a Novel Device to Monitor Sleep and Breathing in the Home, Sleep, vol. 18, No. 2, Feb. 1995, pp. 115-126.

Wilkinson, M. H., et al., Effect of Venous Oxygenation on Arterial Desaturation Rate During Repetitive Apneas in Lambs, Respiration Physiology 101 (19950 321-331.

Williams, et al., Screening for Sleep Apnea Using Pulse Oximetry and A Clinical Score, Chest, 100/3, Sep. pp. 631-635.

Agilent Technologies "M1165/66/67/75/76/77A Component Monitoring System & Agilent M1205a V24 and V26 Manual Part No. M1046-9161L" printed Nov. 2000.

Agilent Technologies "M1165/66/67/75/76/77A Component Monitoring System & Agilent M1205a V24 and V26 Users Reference Manual vol. 2 part No. M1046-9101L" printed Nov. 2000.

* cited by examiner

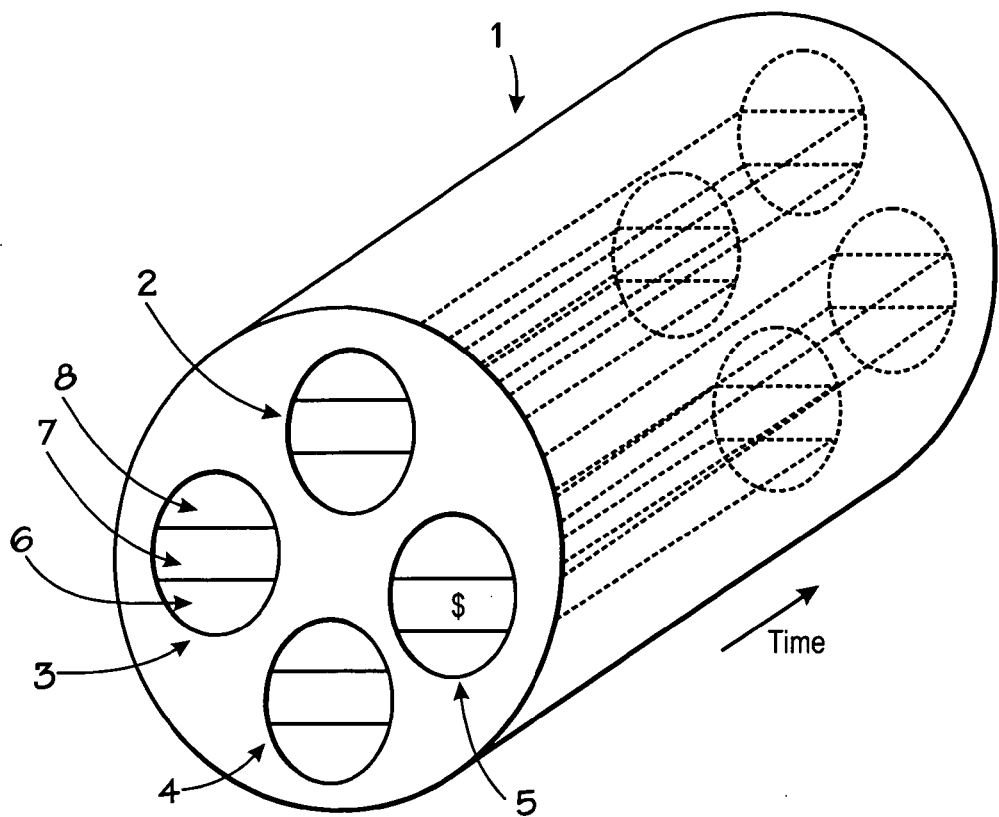
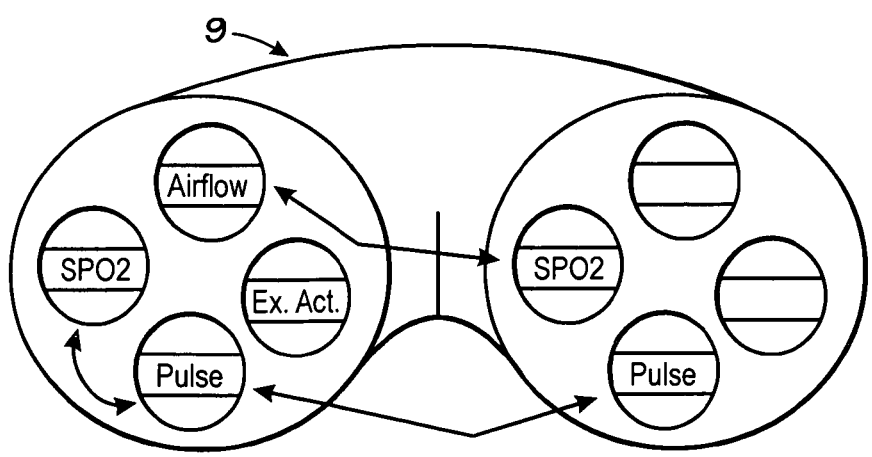
FIG. 4

*channel type (sample rate, lower bound, upper bound)*
*[Transform1 (parameter1] [,... ]) ]*
*[...]*

Capital letters represent channel types as follows:

| Channel Type | Representation Symbol |
|---|---|
| Airflow | 'A' |
| Pulse | 'P' |
| Oximetry | 'O' |

Lower case letters represent transforms as follows:

| Transform | Definition | Representative Symbol |
|---|---|---|
| Reformat | Change a channel from one sample rate to sample rate | 'r' |
| Vertical Scale | Alter the vertical range of values | 'v' |
| Smooth | Alter individual points according to surrounding points | 's' |
| Filter | Method to remove outliers | 'f' |
| Magnitude | Convert to the absolute value of the distance from a reference value | 'm' |
| Derivative | Convert to the value of the slope of the dipole following the point | 'd' |
| Custom | General purpose transformation allowing a point-by-point conversion using the formula: $aY^b + c$ where 'a', 'b' and 'c' are supplied and Y represents the value of the point before transform | 'c' |
| Integrate | Derive a channel from two or more source channels | 'i' |

Transform parameters are wrapped in parenthesis as follow:

| Transform | Parameter | Value Range |
|---|---|---|
| Reformat | Method | 'a' = Average<br>'l' = Lowest<br>'w' = Weighted Average |
|  | Points/Second | Positive Number |
| Vertical Scale | Method | 't' = Truncate<br>'c' = Convert |
|  | Upper Bound | Number |
|  | Upper Bound | Number |
| Smooth | Method | 'a' = Average<br>'l' = Lowest<br>'w' = Weighted Average |
|  | Number of Points | Positive Odd Integer |
| Filter | Method | 'l' = lowest path<br>'h' = highest path<br>'a' = alternative |
| Magnitude | Reference Value | Number |
| Derivative | (No Parameters) | N/A |
| Custom | Multiplier | Number |
|  | Exponent | Number |
|  | Additive | Number |
| Integrate | Method |  |
|  | Channel With Which to Integrate | Defined with valid channel nomenclature |

FIG. 17

| Nomenclature | Definition |
|---|---|
| O(12.5,0,100) | Raw oximetry channel with a sample rate of 12.5 points per second with a lower bound of 0 and an upper bound of 100 |
| O(12.5,0,120)v(t,0,100)r(a,1) | Oximetry channel with a sample rate of 12.5 points per second with a lower pound of 0 and upper bound of 100 reformatted to 1Hz using the average of all points sampled in a second and then smoothed with a 5 second average (5 points at 1Hz) |
| O(12.5,0,100)r(a,1)s(a,5) | Oximetry channel with a sample rate of 12.5 points per second with a lower bound of 0 and upper bound of 100 reformatted to 1 Hz using the average of all points sampled in a second and then smoothed with a 5 second average (5 points at 1 Hz) |
| A(25,-50,50)s(a,5)m(0) | Airflow sampled at 25 Hz with a range between -50 and 50 smoothed with a 0.12 second average (3 points at 25Hz) and transformed to a magnitude plot around the 0 value |
| O(12.5,0,100)r(a,1)s(a,5)i(x, A(25,-50,50)s(a,5)m(0)) | The integration of the two previous examples using the 'x' integration method |

FIG. 18

Basic instability cluster detection algorithm

Let $o_1, o_2,...,o_m$ be the original data points. The data can be converted to a smoother data set, $x_1, x_2,..., x_n$ by using a moving n average of the data points as a 1-4 second average for cluster recognition or as a 15-30 second average for the identification of a pathophysiologic divergence. For the sake of clarity of presentation, assume that $x_i$ is the average of the original data points for the $i^{th}$ second. A *dipole* is defined to be a pair of consecutive data points. Let $d_i = (x_i, x_{i+1})$ be the $i^{th}$ dipole, for $i = 1,2,...,n-1$. The *polarity*, say $p_i$ of the $i^{th}$ dipole is the sign of $x_{i+1} - x_i$ (i.e. $p_i = 1$ if $x_{i+1} > x_i$, $p_i = 0$ if $x_{i+1}$ and $p_i = x_i$ and $p_i = -1$ if $x_{i+1} < x_i$). For the purpose of automatic recognition of user specified, more complex nonlinear waveforms, the data can be converted to a set of dipole slopes, $z_1, z_2,...,z_n$. Let $z_i = (x_{i+1} - x_i)$ be the $i^{th}$ dipole slope, for $i = 1,2,...,n-1$.

To recognize a decline event by applying the iterative slope dipole method according to the present invention, Let, $\{z_1, z_2,...,z_n\}$ be a set of consecutive dipole slopes.
Then $\{z_1, z_2,...,z_n\}$ is a decline if it satisfies the following conditions:
1. $z_1, z_2,...,z_n$ are less than zero i.e., the parameter level of the patient is continually falling over the set of dipole slopes. (This condition will be partially relaxed to adjust for outliers, as by the method described bellow for the linear method).
2. the relationship of $z_1$ to $z_2$, $z_2$ to $z_3$,..., $z_{n-1}$ to $z_n$ is/are specified parameter(s) defining the shape of the decline object, these specified parameters can be derived from the processor based calculations of the dipole slopes made from a user selected consecutive data set or from a set drawn by the user onto a scaled grid.

To recognize a rise event a similar method is applied wherein $z_1, z_2,...,z_n$ are greater than zero. Complex events, which include rise and fall components are built from these more composite objects. Alternatively, a specific magnitude of change along a dipole slope data set can be used to specify a complex object comprised of two composite objects separating at the point of change (a waveform deflection point).

To recognize a decline event by applying the linear method according to the present invention, Let $\{x_i, x_{i+1},...,x_r\}$ be a set of consecutive points and let $s = (x_r - x_i) / (r - i)$ be the overall slope of these points. (The slope could be defined by using linear regression, but this presently preferred definition allows for improved fidelity of the output by allowing rejection based on outlier identification, which will be discussed). Then $\{x_i, x_{i+1},...,x_r\}$ is a decline if it satisfies the following conditions:
3. $x_i > x_{i+1} > ... > x_r$ i.e., the parameter level of the patient is continually falling over the set of points. (This condition will be partially relaxed to adjust for outliers, as described below.)
4. $r - i \geq D_{min}$, where $D_{min}$ is a specified parameter that controls the minimum duration of a decline.
5. $S_{min} \leq S \leq S_{max}$, where $S_{min}$ and $S_{max}$ are parameters that specify the minimum and maximum slope of a decline, respectively.

The set, $\{97, 95, 94, 96, 92, 91, 90, 88\}$, does not satisfy the current definition of a decline even though the overall level of the parameter is clearly falling during this interval. The fourth data point, 96, is an outlier to the overall pattern. In order to recognize this interval as a decline, the first condition must be relaxed to ignore outliers. the modified condition 1 is:
1*. Condition 1 with Outlier Detection
   a. $x_i > x_{i+1}$.
   b. $x_j > x_{j+1}$ or $x_{j+1} > x_{j+2}$ for $j = i+1,..., r-2$.
   c. $x_{r-1} > x_r$.

To recognize a rise event, let $\{x_i, x_{i+1},...,x_r\}$ be a set of consecutive points and let $s = (x_r - x_i) / (r - i)$ be the overall slope of these points. Then $\{x_i, x_{i+1},...,x_r\}$ is a rise if it satisfies the following conditions:
1. $x_i < x_{i+1} < ... < x_r$ i.e. the parameter level of the patient is continually rising over the set of points. (This condition will be partially relaxed to adjust for outliers, as described below.)
2. $r - i \geq D_{min}$, where $D_{min}$ is a specified parameter that controls the minimum duration of rise.
3. $S_{min} \leq S \leq S_{max}$ where $S_{min}$ and $S_{max}$ are parameters that specify the minimum and maximum slope of a decline, respectively.

Similar to declines, the first condition of the definition of a rise is relaxed in order to ignore outliers. The modified condition 1 is:
1*. Condition 1 with Outlier Detection
   a. $x_i < x_{i+1}$.
   b. $x_j < x_{j+1}$ or $x_{j+2}$ $x_{j+2}$ for $j = i+1,..., r-2$.
   c. $x_{r-1} < x_r$.

FIG. 20A

To recognize a negative reciprocation the program iterates through the data and recognize events and then identifies event relationships to define the reciprocations. The system uses polarities (as defined by the direction of parameter movement in a positive or negative direction) to test for condition (1*) rather than testing for greater than or less than. This simplifies the computer code by permitting the recognition of all decline and rise events to be combined in a single routine and ensure that decline events and rise events do not overlap, except that they may share an endpoint. The tables below show how condition (1*) can be implemented using polarities.

Equivalent Condition 1* for Decline event

| | Condition 1* | Equivalent Condition |
|---|---|---|
| a. | $x_i > x_{i+1}$ | $p_i = -1$ |
| b. | $x_j > x_{j+1}$ or $x_{j+1} > x_{j+2}$ | $p_j = -1$ or $p_{j+1} = -1$ |
| c. | $x_{r-1} > x_r$ | $p_{r-1} = -1$ |

Equivalent Condition 1* for Rise event

| | Condition 1* | Equivalent Condition |
|---|---|---|
| a. | $x_i < x_{i+1}$ | $p_i = 1$ |
| b. | $x_j < x_{j+1}$ or $x_{j+1} < x_{j+2}$ | $p_j = -1$ or $p_{j+1} = 1$ |
| c. | $x_{r-1} < x_r$ | $p_{r-1} = 1$ |

The pseudocode for the combined microprocessor method, which recognizes both unipolar decline events and unipolar rise events, is shown below. In this code, E is the set of events found by the method, where each *event* is either a decline or a rise.

```
Event Recognition
i = 1
event_polarity = p₁
for j = 2 to n-2
    if (pⱼ ≠ event_polarity) and (pⱼ₊₁ ≠ event_polarity)
        r = j
        X = {xᵢ,...,xᵣ}
        if event_polarity = 1
            Add X to E if it satisfies rise conditions (2) and (3)
        elseif event_polarity = -1
            Add X to E if it satisfies decline conditions (2) and (3)
        endif
        i = j
        event_polarity = pⱼ
    endif
endfor
Add X = {xᵢ,...,xₙ} to E if it satisfies either the rise or decline conditions
```

Next, A specific pattern is recognized by identifying a certain sequence of consecutive events, as defined above, which comply with specific spatial relationships. For Example, a negative reciprocation is recognized when a decline event, say $D = \{x_i,...,x_j\}$, together with a rise event, say $R = \{x_k,...,x_m\}$, that closely follows it. In particular D and R must satisfy $k-j \leq t_{dr}$ where $t_{dr}$ is a parameter, specified by the user, that controls the maximum amount of time between D and R to Qualify as a negative reciprocation.

The exemplary pseudocode for the microprocessor system to recognize a negative reciprocation is shown bellow. Let $E = \{E_1, E_2,...,E_q\}$ be the set of events (decline events and rise events) found by the event recognition method, and let Dr be the set of a negative reciprocation.

```
Negative Reciprocation
for h = 1 to q-1
    Let D = {xᵢ,...,xⱼ} be the event Eₕ
    if D is a decline event
        Let R = {xₖ,...,xₘ} be the event Eₕ₊₁
        if R is a rise event
            gap = K-j
            if gap ≤ t_dr
                Add (D,R) to the list, DR, of negative patterns
            endif
        endif
    endif
endfor
```

FIG. 20b

As noted, a cluster is a set of consecutive negative or positive reciprocation that appear close together. In particular, let $C = \{DR_i, DR_{i+1},...,DR_k\}$ be a set of consecutive negative reciprocations, $s_j$ be the time at which $DR_j$ starts, and $e_j$ be the time at which $DR_j$ end. Then $C$ is a cluster if it satisfies the following conditions:
1. $s_{j+1} - e_j \leq t_c$ for $j = i,...,k-1$, where $t_c$ is a parameter, specified by the user, that controls the maximum amount of time between consecutive negative reciprocations in a cluster.
2. $k - i + 1 \geq c_{min}$ where $c_{min}$ is a parameter, specified by the user, that controls the minimum number of negative reciprocations in a cluster The pseudocode for the algorithm to recognize clusters of negative reciprocations is shown below. Let $DR = \{DR_1, DR_2,...,DR_r\}$ be the set of negative reciprocations found by the above pattern recognition method.

```
            Cluster Recognition (of negative reciprocations)
f = 1;
    for h = 2:r
            Let R = {x_1,...,x_m} be the rise in DR_{h-1}
            Let D = {x_i,...,x_j} be the decline in DR_h
            gap = i-m
            if gap > t_c
                    g = h-1
                    if g - f + 1 ≥ c_min
                    Add DR_f, DR_{f+1},..., DR_g to the list of clusters
                    endif
                    f = h
            endif
    endfor
    g = r
    if g - f + 1 ≥ c_min
            Add DR_f, DR_{f+1},..., DR_g to the list of clusters
    endif
```

FIG. 20C ns or human error. In summary, it is critical to accurately and timely recognize airway and ventilation instability and adverse medication responses in hospitalized patients.

CENTRALIZED HOSPITAL MONITORING SYSTEM FOR AUTOMATICALLY DETECTING UPPER AIRWAY INSTABILITY AND FOR PREVENTING AND ABORTING ADVERSE DRUG REACTIONS

This application claims priority of provisional applications U.S. Ser. Nos. 60/291,691 and 60/291,687, both filed 17 May 2001 and provisional application U.S. Ser. No. 60/295,484, filed 1 Jun. 2001, the disclosures and contents of each of which is incorporated by reference as if completely disclosed herein.

FIELD OF THE INVENTION

This invention relates to centralized hospital monitoring systems and particular to the organization, analysis, and automatic detection of patterns indicative of upper airway instability during sleep, deep sedation, and analgesia.

BACKGROUND AND SUMMARY OF THE INVENTION

The high number of unnecessary deaths in the hospital due to errors related to pharmaceutical administration such as sedative and narcotics has been a recent focus of US government studies and much discussion in the literature and press. The present inventors recognized that these adverse events occur not only due to improper dosage of medications or the administration of drug to the wrong patient, as has been recently highlighted in the medical literature and press, but also due to failure to recognize complex patterns along monitored outputs (such as those shown in FIG. 2) indicative of patient instability before, during, and after the administration of such medications. These patterns can provide evidence that a given dose of medication, which may appear to be correct according to the Physician's Desk Reference or other source, may be too much for a given patient in a given physiologic state. Administration of "standard acceptable dosages" to patients with potentially unstable physiology can produce an insidious and deadly occurrence of relative drug excess, which will not be prevented by simple computer matching of patient name and drug. Further, the present inventors recognized that failure to timely interrupt infusion upon the occurrence of physiologic instability represented a major cause of death. The timely recognition of a change in the pattern of the patient monitored output can be seen as the last opportunity to correct the mistake of wrong drug, wrong dose, wrong patient, relative drug excess, or a potentially fatal idiosyncratic or allergic reaction.

In hospitals, throughout the United States monitored patients are experiencing profound physiologic instability before and during medication infusion producing patterns as shown in FIG. 2 and yet still are being subjected to continuous infusion of further destabilizing and potentially deadly narcotics and sedation simply because the hospital monitors do not recognize the patterns nor are they programmed to warn the hospital worker or to lock out the infusion based on such recognition. An example of such instability and a system and method according to the present invention for identification of such patterns follows although, upon this teaching, the skilled artisan will recognize that there are many modifications within the scope of this teaching, which will allow the recognition of other patterns of instability A major factor in the development of respiratory failure (one of the most common causes of death in the hospital) is airway instability, which results in airway collapse during sedation, stroke, narcotic administration, or stupor. As illustrated in FIGS. 3a and 3b, such collapse occurs in dynamic cycles called airway instability clusters affecting a range of physiologic signals. Subgroups of patients in the hospital are at considerable risk from this type of instability. In addition patients with otherwise relatively stable airways may have instability induced by sedation or narcotics. The present inventors recognized that it is critical that this instability be recognized in real time in the hospital so that the dose can be adjusted or the drug withheld upon the recognition of this development. They also realized that it is critical to use the opportunity afforded by hospitalization in association with hospital monitoring to automatically evaluate for the common disorder induced by upper airway instability—obstructive sleep apnea. Conventional central patient monitors are neither configured to provide interpretive recognition the cluster patterns indicative of airway and ventilation instability nor to provide interpretative recognition of the relationship between and along airway instability clusters. In fact, such monitors often apply averaging algorithms, which attenuate the clusters. For these reasons thousands of patients each day enter and leave hospital-monitored units with unrecognized sleep apnea and ventilation and airway instability.

This failure of conventional hospital based patient monitors to timely and/or automatically detect cluster patterns indicative of airway instability can be seen as a major health care deficiency indicative of a long unsatisfied need. Because obstructive sleep apnea, a condition derived from airway instability, is so common, the consequence of the failure of conventional hospital monitors to routinely recognize upper airway instability clusters means that many of patients with this disorder will never be diagnosed in their lifetime. For these patients, the diagnostic opportunity was missed and the health implications and risk of complications associated with undiagnosed airway instability and sleep apnea will persist in this group throughout the rest of their life. A second group of patients will have a complication in the hospital due to the failure to timely recognize airway instability. Without recognition of the inherent instability, a patient may be extubated too early after surgery or given too much narcotic (the right drug, the right patient, the ordered dose but unknowingly a "relative drug excess"). Indeed until clusters indicative of airway instability are routinely recognized by hospital monitors, the true incidence of respiratory failure, arrest, and/or death related to the administration of IV sedation and narcotics to patients in the hospital with airway instability will never be known but the number is probably in the tens of thousands each year and airway instability is just one example of the types of physiologic instability which are not automatically characterized by central hospital systems.

To understand the criticality of recognizing airway instability in real-time it is important to consider the significance of the combined effect that oxygen therapy and narcotics or sedation may have in the patient care environment in the hospital, for example, in the management of a post-operative obese patient after upper abdominal surgery. Such a patient may be at particular risk for increased airway instability in association with narcotic therapy in the through 3rd post-operative day due to sleep deprivation, airway edema, and sedation. Furthermore, in the second and third postoperative day monitoring the vigilance of hospital personnel may diminish due to perceived stability, and rebound rapid eye movement (REM) sleep which can increase upper airway instability may occur due to antecedent sleep deprivation. Indeed, many of these patients have significant sleep apnea prior to admission to the hospital which is unknown to the surgeon or the anesthesiologist due to the subtly of symptoms. Such patients, even with severe sleep apnea, are relatively safe at home because of an intact arousal response; however, in the hospital, narcotics and sedatives often remove this "safety net. The administration of post-operative narcotics can shift the arousal curve to the right and this can significantly increase the danger of airway instability and, therefore, place the patient at substantial risk. Many of these patients are placed on electrocardiographic monitoring but the alarms are generally set at high and low limits. Hypoxemia, induced by airway instability generally does not generally produce marked levels of tachycardia; therefore, airway instability is poorly identified by simple electrocardiographic monitoring without the identification of specific pattern of clusters of the pulse rate. In addition, simple oximetry evaluation is also a poor method to identify airway instability. Conventional hospital oximeters often have averaging intervals, which attenuate the dynamic desaturations. Even when the clustered desaturations occur they are often thought to represent false alarms because they are brief. When desaturations are recognized as potentially real this often results in the simple and often misguided addition of nasal oxygen. However, nasal oxygen may prolong the apneas and potentially increase functional airway instability. From a monitoring perspective, the addition of oxygen therapy can be seen to potentially hide the presence of significant airway instability by attenuation of the level of desaturation and reduction in the effectiveness of the oximeter as a monitoring tool in the diagnosis of this disorder.

Oxygen and sedatives can be seen as a deadly combination in patients with severely unstable airways since the sedatives increase the apneas and the oxygen hides them from the oximeter. For all these reasons, as will be shown, according to the present invention, it is critical to monitor patients with increased risk of airway instability for the specific monomorphic and polymorphic cluster patterns as will be discussed, during the administration of narcotics or sedatives.

Having identified, supra, the long and critical need, a discussion of the background physiology of upper airway instability will first be provided.

The central drive to breath, which is suppressed by sedatives or narcotics, basically controls two critical muscle groups. The upper airway "dilator muscles" and the diaphragm "pump muscles". The tone of both these muscle groups must be coordinated. A fall in afferent output from the brain controller to the airway dilators results in upper airway collapse. Alternatively, a fall in afferent output to the pump muscles causes hypoventilation.

Two major factors contribute to respiratory arrest in the presence of narcotic administration and sedation. The first and most traditionally considered potential effect of narcotics or sedation is the suppression by the narcotic or sedative of the brains afferent output to pump muscle such as the diaphragm and chest wall, resulting in inadequate tidal volume and associated fall in minute ventilation and a progressive rise in carbon dioxide levels. The rise in carbon dioxide levels causes further suppression of the arousal response, therefore, potentially causing respiratory arrest. This first cause of respiratory arrest associated with sedation or narcotics has been the primary focus of previous efforts to monitor patients postoperatively for the purpose of minimization of respiratory arrests. Both oximetry and tidal CO2 monitoring have been used to attempt to identify and prevent this development. However, in the presence of oxygen administration, oximetry is a poor indicator of ventilation. In addition, patients may have a combined cause of ventilation failure induce by the presence of both upper airway instability and decreased diaphragm output as will be discussed, this complicates the output patterns of CO2 monitors making recognition of evolving respiratory failure due to hypoventilation more difficult for conventional threshold alarm based systems.

The second factor causing respiratory arrest due to narcotics or sedatives relates to depression of the brains afferent output to upper airway dilator muscles causing a reduction in upper airway tone. This reduction in airway tone results in dynamic airway instability and precipitates monomorphic cluster cycles of airway collapse and recovery associated with the arousal response as the patient engages in a recurrent and cyclic process of arousal based rescue from each airway collapse. If, despite the development of significant cluster of airway collapse, the narcotic administration or sedation is continued, this can lead to further prolongation of the apneas, progression to dangerous polymorphic desaturation, and eventual respiratory arrest. There is, therefore, a dynamic interaction between suppression of respiratory drive, which results in hypoventilation and suppression of respiratory drive, which results in upper airway instability. At any given time, a patient may have a greater degree of upper airway instability or a greater degree of hypoventilation. The relative combination of these two events will determine the patterns of the output of the monitor.

Unfortunately, this has been one of the major limitations of carbon dioxide monitoring. The patients with significant upper airway obstruction are also the same patients who develop significant hypoventilation. The upper airway obstruction may result in drop out of the nasal carbon dioxide signal due to both the upper airway obstruction, on one hand, or due to conversion from nasal to oral breathing during a recovery from the upper airway obstruction, on the other hand. Although breath by breath monitoring may show evidence of apnea, conversion from nasal to oral breathing can reduce the ability of the CO2 monitor to identify even severe hypoventilation in association with upper airway obstruction, especially if the signal is averaged or sampled at a low rate. For this reason, conventional tidal CO2 monitoring when applied with conventional monitors without out cluster pattern recognition may be least effective when applied to patients at greatest risk, that is, those patients with combined upper airway instability and hypoventilation. The present inventors recognized that this unique physiologic process of reentry of airway collapse could be exploited to provide a system and method for the recognition of the waveform patterns of airway instability. Several early embodiments are described in U.S. Pat. No. 6,223,064 (which is assigned to the present inventor, the disclosure and the entire contents of which are incorporated by reference is if completely disclosed herein). These systems and methods exploit the underlying cyclic physiologic process, which drives the perpetuation of a cluster of airway closures, to provide automatic recognition and indication of upper airway instability in real time. As discussed, the underlying cyclic process, which defines the behavior of the unstable upper airway, is associated with precipitous changes in ventilation and attendant precipitous changes in monitored parameters, which reflect and/or are induced by such ventilation changes. For example, cycling episodes of airway collapse and recovery produces sequential precipitous changes in waveform output defining analogous cluster waveforms in the time series of: oximetry derived pulse, airflow amplitude or/and tidal frequency, the oximetry $SpO_2$, the chest wall impedance and/or motion, EKG pulse rate, and/or R to R interval, EEG (due to clustering of arousals), EMG due to clustering of motor response to arousals), systolic time intervals, and other parameters which vary with the brisk clustered cycles of apnea and recovery. EEG is readily available in the hospital as BIS monitors, according to the present invention the detection of clusters of alpha or high amplitude, mixed frequency arousals in clusters is very useful to indicate the potential presence of airway instability. According to the present invention, any one of these parameters singularly or in combination can be used in the hospital to detect either the absolute presence of airway instability or to provide evidence of probable airway instability so that hospital personnel know that additional testing should be applied.

Conventionally, in the hospital, the analysis of one or more time series datasets is widely used to characterize the behavior of physiologic systems and to identify the occurrence adverse events. One basic conventional hospital montage commonly connected to a central monitor by telemetry includes electrocardiogram (EKG), pulse oximetry, and chest wall impedance). Using this grouping of monitors, the human physiologic system produces a large array of highly interactive time series outputs, the dynamic relational configurations of which have substantial relevance when monitored over both brief and long time intervals. The present inventors recognized that multiple unique patterns of airway instability were present along the time series and that these different patterns could be identified to provide an interpretive output such a textual output and/or other alarm. In addition, the present inventors recognized that the complexity and time course variability of these patterns commonly overwhelms hospital workers so that timely intervention is often not applied, resulting in unnecessary death or patient injury. The inventors further recognized that the processed based recognition of these patterns could be used to take action in the interest of the health of the patient, such as automatically lock out narcotic or sedation medication or increase the level and/or type of ventilation support. They also recognized that combined central and satellite processing systems such as those used in the hospital based system discussed supra, could be modified to provide such automatic recognition and to provide such output and/or take such action to improve the health care of patients such as automatically locking out a drug infusion upon the recognition of the interval development of an unstable pattern potentially indicative of an adverse drug reaction or titration of continuous positive pressure devices. The invention also provides a method of doing business to improve the sale of patient monitoring systems, CPAP, and disposable probes for use with the monitors.

According one aspect of the present invention, the recognition of sequential precipitous events or pathophysiologic patterns can be achieved by analyzing the spatial and/or temporal relationships between at least a portion of a waveform of a physiology parameter, (such as, for example, those listed supra), induced by at least a first episode of airway collapse and at least a portion of a waveform induced by at least a second episode of airway collapse. This can include the recognition of a pattern indicative of a cluster, which can compromise a high count of apneas with specified identifying features which occur within a short time interval along said waveform (such as 3 or more apneas within about 5–10 minutes) and/or can include the identification of a waveform pattern defined by closely spaced episodes of airway collapse defining waveform clusters. Further, the recognition can include the identification of a spatial and/or temporal relationship defined by waveform clusters, which are generated by closely spaced sequential apneas due to cycling upper airway collapse and recovery.

According to another aspect of the invention, the patterns of these complex interactive signals and the data sets defining path physiologic upper airway instability are characterized by organizing the time series into an ascending hierarchy of objects (which in one preferred embodiment are substantially in the time domain), ordering these objects into a relational data matrix and then recognizing the complex reciprocations across time series and across scales and by applying an expert system to that set of highly organized set of objects.

For the purpose of organizing and identifying physiologic datasets, according to the present invention a fundamental dynamic time series object is identified and characterized, which possesses a unique symmetry of scale. The inventors call this object a "physiologic reciprocation". For the purpose of pattern recognition, according to the present invention, a physiologic reciprocation is a fundamental variation time series output generated by an organ, an organ system, and/or an entire organism, which is at least partially reversed within a specified interval. According to the present invention reciprocations, as recognized by the processor, are widely scalable across substantially all fundamental output patterns of organ function and physiologic control. The present inventors recognized that an scaleable system which recognized and analyzed reciprocations along a time series, across different scales of the time series, and between different scales of different contemporaneously derived time series, could be used to readily identify specific dynamic physiologic patterns of interaction defining both different states of disease and health. Further, the present inventors recognized that, for the purpose of processor based pattern recognition, human physiologic function (and dysfunction) can be characterized by defining and recognizing a object hierarchy of physiologic reciprocations ordered into an ascending, inheritance based relational timed data matrix.

Using the above discoveries the present inventors recognized that typical standard central hospital monitors including those with wireless capabilities (such as the system described for example U.S. Pat. No. 6,364,834) and outpatient holter type monitors can be improved to provide automatic recognition of airway instability and sleep apnea and to provide an automatic visual or audible indication of the presence of such clusters and further to provide a visual or audible output and severity of this disorder thereby rendering the timely recognition and diagnosis of upper airway instability and obstructive sleep apnea as routine and automatic in the hospital as the diagnosis of other common diseases such as hypertension.

FIG. 3a illustrates the reentry process driving the propagation of airway instability reentry clusters. The physiologic basis for these clusters has been previously described in U.S. Pat. Nos. 5,891,023 and 6,223,064 and provisional application No. 60/291,691 (the entire contents of each of which are incorporated by reference as if completely disclosed herein). This cycle is present when the airway is unstable but the patient is capable of arousal. In this situation, in the sleeping or sedated patient, upon collapse of the airway, the patient does not simply die, she rescues herself and precipitously opens the airway to recover by hypoventilation, however, if the airway instability remains after the arousal and rescue is over, the airway collapses again, only to be rescued again thereby producing a cluster of closely spaced apneas with distinct spatial, frequency and temporal waveform relationships between and within apneas wherein the physiologic process reenters again and again to produce a clustered output. According to the present invention, an airway instability cluster is comprised of a plurality (two or more) of closely spaced apneas or hypopneas but the use of 3 or more apneas is preferred. The present invention includes (but is not limited to) recognition of airway instability clusters in oxygen saturation, pulse, chest wall impedance, blood pressure, airflow (including but not limited to exhaled carbon dioxide and air temperature), nasal and oral pressure, systolic time intervals, electrocardiograph tracings (including pulse rate and R to R interval plots), timed plots of ST segment position, chest wall and/or abdominal movements (as by strain gauge, impendence, or other methods), electromyography (EMG), and electroencephalography (EEG). For all of these waveforms the basic underlying cluster pattern is similar and the same basic presently preferred cluster pattern recognition system and method, according to the present invention, can be applied to recognize them.

According to one aspect of the invention a microprocessor system is provided for the recognition of specific dynamic patterns of interaction between a plurality of corresponding and related time series, the system comprises a processor programmed to; process a first time series to produce a lower-level time series of sequential time series fragments derived from the first time series, process the lower-level time series to produce a higher-level time series comprised of sequential time series fragments from the lower-level time series, process a second time series, the second time series being related to the first time series, produce a second lower-level time series of sequential time series fragments derived from the second time series, and identify a dynamic pattern of interaction between the first time series and the second time series.

The system can be further programmed to process the lower-level time series of the second time series to; produce a higher-level time series derived from sequential time series fragments of the second lower-level time series. The system can be programmed to process a third time-series, the third time series being related to at least one of the first and the second time series, to produce a third lower-level time series of sequential time series fragments derived from said third time series. The system can be programmed to process the higher-level time series to produce a complex-level time series derived from sequential time series fragments of said higher-level time series. The time series fragments of the first and second time series can be stored in a relational database, the fragments of the higher-level time series can comprise objects, the objects inheriting the characteristics of the objects of the lower-level time series from which they are derived. The first and second time series can comprise datasets of physiologic data points and the system can comprise a patient monitoring system wherein the dynamic pattern of interaction comprises convergent clusters of pathologic reciprocations.

It is the purpose of the present invention to provide a diagnostic system, which can convert conventional hospital-based central telemetry and hard wired monitoring systems and portable home systems to provide processor based recognition of airway instability through the recognition of patterns of closely spaced reciprocations and/or events induced by apneas and/or hypopneas both in real time and in overnight interpretive format and which can automatically lock-out narcotic infusion upon recognition of patterns of instability.

It is the purpose of the present invention to provide a system, which identifies, maps, and links waveform clusters of airway instability from simultaneously derived timed signals of multiple parameters including chest wall movement, pulse, airflow, exhaled carbon dioxide, systolic time intervals, oxygen saturation, EKG-ST segment level, EEG, EMG, and other parameters to enhance the real-time and overnight diagnosis of airway instability.

It is further the purpose of the present invention to provide a system to provide a graded index and/or indication of patterns of airway instability.

It is further the purpose of the present invention to provide a system, which provides characterization of different types of patterns of ventilation and/or upper airway instability.

It is further the purpose of the present invention to provide a system, which provides characterization and/or differentiation of different types of patterns such as monomorphic, polymorphic, and combined patterns of instability.

It is further the purpose of the present invention to provide a system, which provides characterization to output an indication of the type of pattern identified by the processor so that a decision relevant the probability of success of auto titration with CPAP and/or BIPAP can be made.

It is further the purpose of the present invention to provide timely, real-time indication such as a warning or alarm of the presence of airway instability clusters so that nurses can be aware of the presence of a potentially dangerous instability of the upper airway during titration of sedatives and/or narcotics.

It is further the purpose of the present invention to provide a system for the recognition of airway instability for combined cluster mapping of a timed dataset of nasal oral pressure with tidal CO2 to identify clusters of conversion from nasal to oral breathing and to optimally recognize clusters indicative of airway instability in association with tidal CO2 measurement indicative of hypoventilation.

It is the purpose of the present invention to provide an iterative object oriented waveform processing system, which can characterize, organize, and compare multiple signal levels across a plurality of signals by dividing each waveform level of each signal into objects for discretionary comparison within a relational database, object database or object-relational database It is further the purpose of the present invention to provide a system, which automatically triggers lockout of medication infusion based on the recognition of an adverse pattern of instability along at least one timed dataset output.

It is another aspect of the present invention to provide a system that automatically customizes treatment algorithms or diagnostic algorithms based on the analysis of waveforms of the monitored parameters.

It is further the purpose of the present invention to provide a system, which provides recognition and characterization of physiologic reciprocations across different time series scales.

It is further the purpose of the present invention to provide a system, which automatically triggers testing (and comparison of the output) of a secondary intermittently testing monitor upon the recognition of patterns indicative of physiologic instability.

It is further the purpose of the present invention to provide real time protection to patients against adverse drug and to provide a data matrix comprising matched time series of physiologic signals with a time series of drug infusion so that hospital personnel can readily match specific patterns of pathophysiologic perturbations to specific types of medications and ranges of medication dosage for patients hospital wide.

BRIEF DESCRIPTION OF THE DRAWINGS

FIG. 4 show a shows a three-dimensional representation of the cylindrical data matrix comprised of corresponding, streaming, time series of objects from four different timed data sets, with each of the four data sets divided into an ascending hierarchy of 3 levels.

FIG. 10e shows a 19.2-minute segment of a time series of oximetry illustrating a modest variation of the peaks of reciprocations with negative reciprocations of the nadirs each said reciprocation becoming more negative. This peak variation is consistent with a mild polymorphic cluster. Note that the variations of the nadirs can be indicative of an important instability and decline in arousal threshold despite a complete or nearly complete arousal response. This pattern is automatically recognized according to the present invention to provide an output indication or to take action such as to lock out medication.

FIG. 17 shows one presently preferred nomenclature for the exemplary parameters of airflow, pulse, and oxygen saturation. Illustrative examples of designation by this nomenclature are shown in FIG. 18.

DESCRIPTION OF THE PRESENTLY PREFERRED EMBODIMENTS

Figure 1:
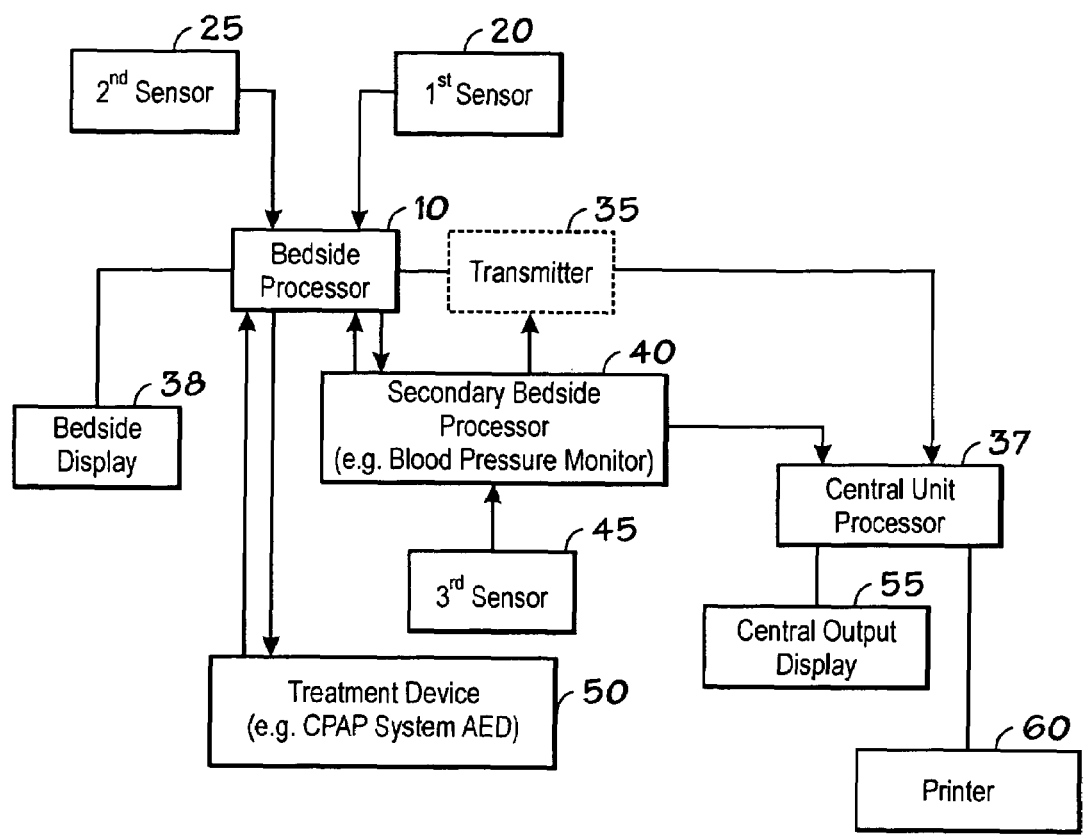
FIG. 1 shows a schematic of a hospital central processing system for outputting and/or taking action based on the analysis of the time series processing according to the present invention.

One presently preferred system for processing, analyzing and acting on a time series of multi-signal objects is shown in FIG. 1. The examples provided herein show the application of this system for real time detection, monitoring, and treatment of upper airway and ventilation instability although the present invention is useful for detecting a broad range of patterns and instabilities (as described in co pending. The system includes a portable bedside processor 5 preferably having at least a first sensor 20 and a second sensor 25, which preferably provide input for at least two of the signals discussed supra. The system includes a transmitter 35 to a central processing unit 37. The bedside processor 5 preferably includes an output screen 38, which provides the nurse with a bedside indication of the sensor output. The bedside processors can be connected to a controller of a treatment or stimulation device 50, which can include a drug delivery system such as a syringe pump, a positive pressure ventilation device, an automatic defibrillator, a tactile stimulator, the processor itself, to adjust the analysis of the time-series inputs. The central unit 37 preferably includes as output screen 55 and printer 60 for generating a hard copy for physician interpretation. According to present invention, as will be discussed in detail, the system thereby allows recognition of airway instability, complications related to such instability, and pathophysiologic divergence in real time from a single or multiple inputs. The bedside processor is preferably connected to a secondary processor 40 which can be a unit, which takes action such as locking out a medication infusion, performing measurements intermittently and/or on demand such as a non-invasive blood pressure monitor or an ex-vivo monitor, which draws blood into contact with a sensor on demand for testing to derive data points for addition to the multi-signal objects. The secondary processor 40 includes at least one sensor or controller 45. The output of the bedside processor can either be transmitted to the central processor 37 or to the bedside monitor 5 to render a new object output, action, or analysis.

In one example the occurrence of a dynamic clustering of apneas can be identified and the infusion pump (which can be for example a patient controlled analgesia (PCA) device can be automatically locked out to prevent further infusion and an output such as "Caution—pattern suggestive of mild upper airway instability at dose of 1 mg Morphine." If in this example the nurse increases the dose to 2 miligram and the pattern shows an increase in severity an output such as "Pattern suggestive of moderated upper airway instability at dose of 2 mg/hr. of Morphine-morphine locked out". To maintain Morphine dose at the 2 mg. level for this patient, the nurse or physician would have to override the lockout and preferably document the reason for override. Upon an override the processor then tracks the severity of the clusters and if the clusters reaches an additional severity threshold an output such as "Severe upper airway instability—Morphine locked out" is provided. According to the present invention the onset of the drug administration is recognized by the central processor and the dose administered becomes a time series, which can then be matched to the patterns of the monitored physiologic time series. In addition to real time protection, the data matrix comprising matched time series of physiologic signals with a time series of drug infusion provides an ability for hospital personnel to readily match specific patterns of pathophysiologic perturbations to specific types of medications and ranges of medication dosage for patients hospital wide.

Figure 2:
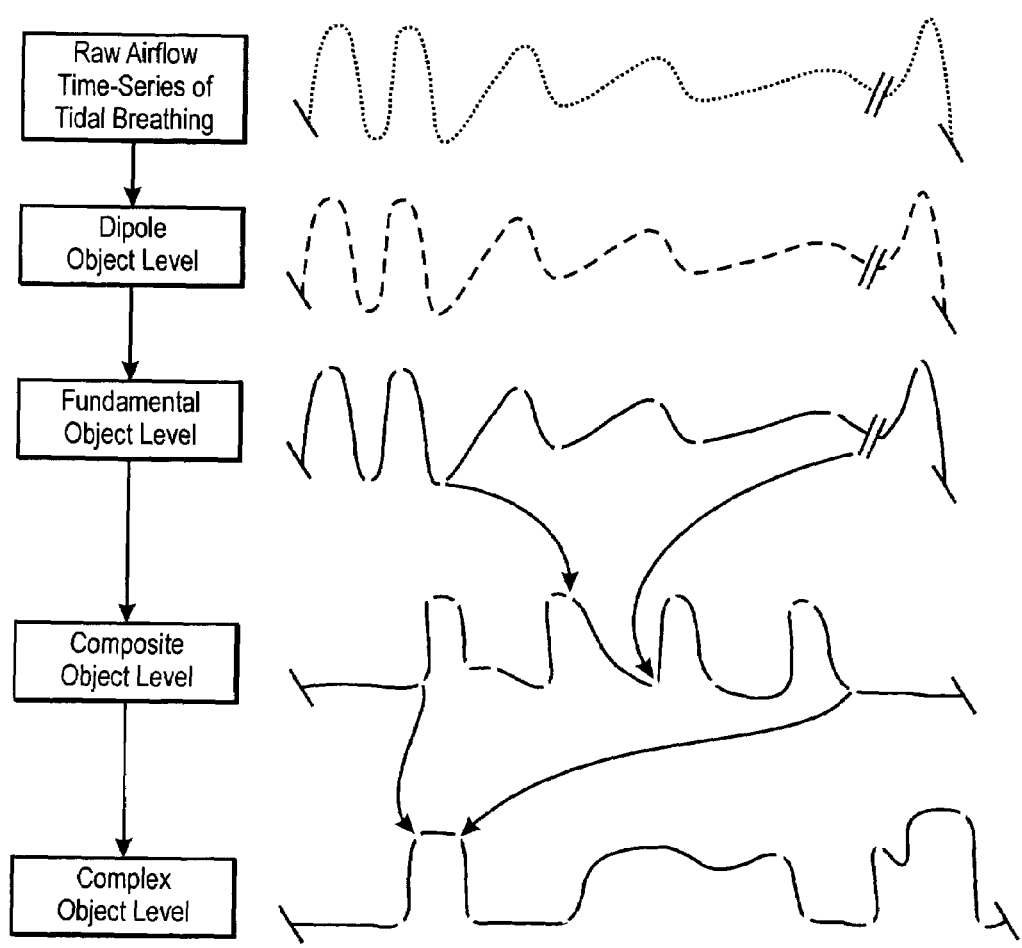
FIG. 2 shows the organization of airflow waveforms into ascending object levels identifying pathophysiologic reciprocations, which demonstrate recognizable symmetry of scale according to the present invention. Note that, according to the present invention, reciprocations at the complex and composite levels inherit the reciprocations from the levels below them in ascending order.

FIG. 2 illustrates the ascending object processing levels according to the present invention, which are next applied to order the objects to recognize the patterns which are identified by the system of FIG. 1 to provide an automatic indication and/or action based a pattern indicative of an adverse physiologic occurrence. In the preferred embodiment, these levels are defined for each signal and comparisons can be made across different levels between different signals. Physiologic reciprocations are identified (if present) and characterized at each level. In FIG. 2 the first level is comprised of the raw data set. The data from this first level are then converted by the processor into a sequence of fundamental segments called dipoles to form the second fundamental object level. In one embodiment, all of the objects, which will ultimately define complex multi-signal objects, are comprised of these sequential fundamental objects having the simple characteristics of slope, polarity, and duration. At this level, the dipoles are used to render the next level, called the "composite object level".

The composite object level is comprised of sequential and overlapping composite objects, and particularly reciprocations, which are composed, of a specific sequence of dipoles as defined by selected criteria. Each of these composite objects has similar primary characteristics of a slope, duration, and polarity to the fundamental objects. However, for the composite objects, the characteristic of slope can comprise a time series characteristic given as a slope dataset. The composite object level also has the characteristic of "intervening interval time-series" defined by a time series of the intervals between the recognized or selected composite objects. At this level a wide range of discretionary index characteristics can be derived from the comparison of basic characteristics of composite objects. Examples of such index characteristics include; a "shape characteristic" as derived from any specified portion of the slope dataset of the object, a "positional characteristic" as derived from, for example, the value of the lowest or highest points of the object, or a "dimensional value characteristic" as derived by calculating the absolute difference between specified data points such as the value of the lowest and the highest values of the object, or a "frequency characteristic" such as may be derived from performing a Fourier transform on the dataset of the object.

The next analysis level is called the "complex object level". In this level, each sequential complex object comprises plurality of composite objects meeting specific criteria. According to the present invention, the patterns of reciprocations at the complex level are representative of a balance between physiologic perturbation and the control. As such they are useful to characterize the integrity of control of the organism as well as the severity and character of the perturbation. According to the present invention, complex physiologic reciprocations are generally derived from composite level reciprocations and inherit their characteristics. Therefore a complex object (such as a recovery object) inherits the composite (tidal breath) reciprocations from which it is derived and this is exploited by the system as will be discussed. Complex objects have the same categories of primary characteristics and derived index characteristics as a composite object. A complex object also has the additional characteristics of "composite object frequency" or "composite object order" which can be used as search criteria as part of an overlaid expert system. These can be defined by a selected frequency or order of composite object types, which are specified as defining a given complex object. A complex object also has additional higher-level characteristics defined by the time-series of the shapes, dimensional values, and positional characteristics of its component composite objects. As described for the composite objects, similar index characteristics of the complex objects can be derived from these characteristics for example; a complex object can be derived as a cluster of composite level reciprocations.

Figure 10A:
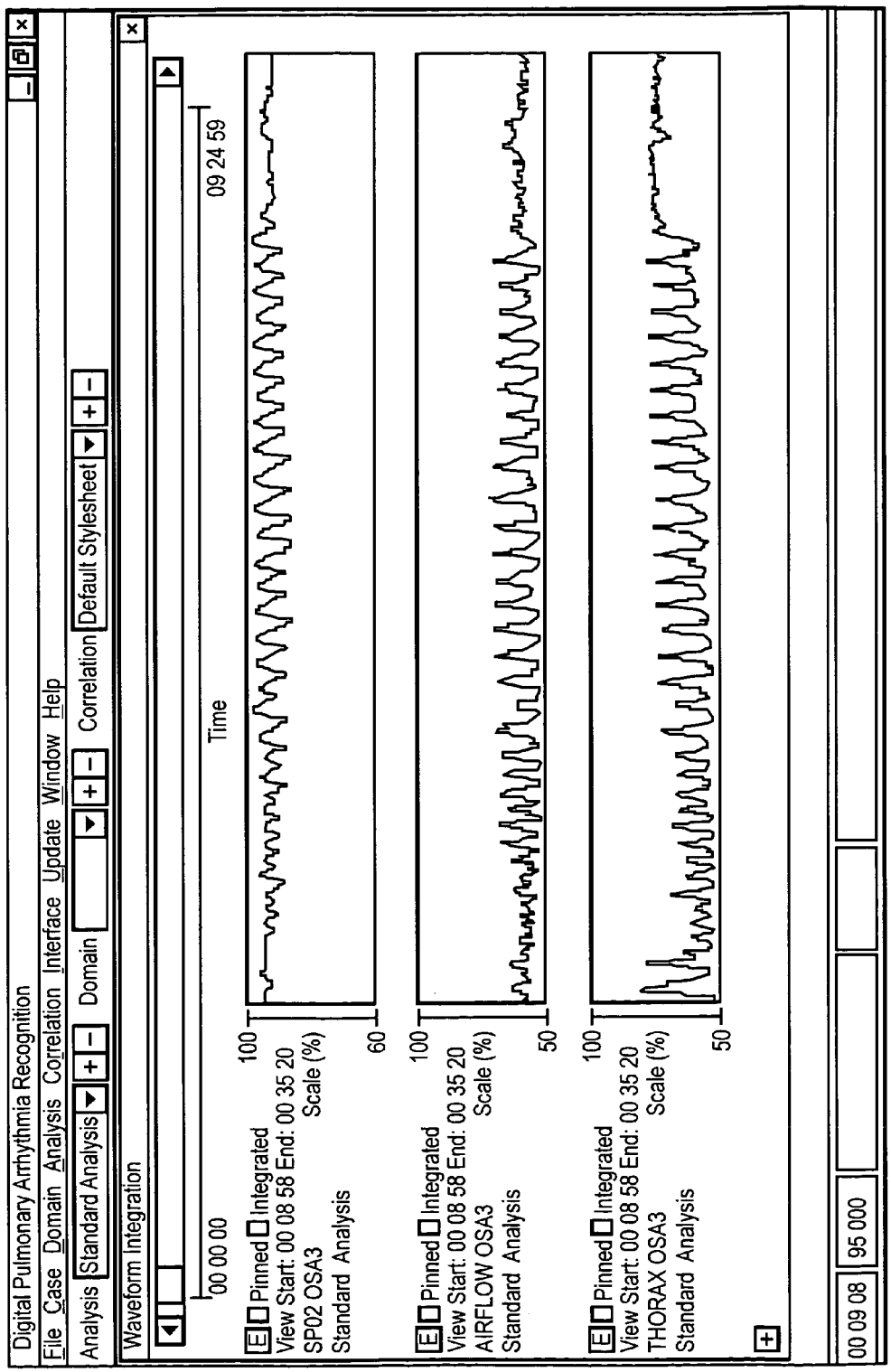
FIG. 10a shows a typical monomorphic airway instability cluster along times series of oximetry, airflow, and thorax movement

In a further example a complex level reciprocation given by a time series of positional characteristic along a clustered grouping of sequential composite objects (such a a reciprocation object derived of sequential nadir points or characteristics of composite level reciprocations of a cluster object at the complex level) can be readily identified and characterized. FIG. 10f shows a superimposed cluster of negative reciprocations of the reciprocation nadirs. Initial fall portions of a severe negative reciprocations of the nadirs of airway instability clusters are shown in FIGS. 10d and 10e and in one presently preferred embodiment these are automatically recognized and indexed relevant magnitude and slope of the decline to provide an output or take action as previous discussed. The present inventors recognized that such a patterns can indicate a high degree of instability of the arousal threshold in relation to a given level of oxygen saturation. This may indicate that other factors are dominating relevant the arousal threshold (such as $CO_2$). However, this negative reciprocation (like virtually all physiologic reciprocations) is indicative of the function and integrity of a control system. As such a severely negative reciprocation of the nadirs (or the initial decline component as shown in FIGS. 10c and 10d) can indicate a dangerous attenuation of the control system defining the arousal threshold (as due to narcotics, sedation, a change in sleep stage, or simply a generally less stable arousal control system). In the alternative, a reciprocation of the peak characteristics of such clusters may be identified (or again the initial decline component as shown in FIGS. 10c and 10d). The inventors recognized that this pattern can be indicative of an inadequate and/or attenuated arousal response so that the clustered reciprocations which exhibit the falling peaks are not incomplete. The identification of one or more severe negative reciprocations of the peaks or the decline component alone of such reciprocations can provide important evidence of inadequate arousal response as can be induced by narcotics and/or a superimposed hypoventilation disorder. Such patterns inside patterns (i.e. objects inside objects) are readily recognized according to the present invention along a single level and across levels, and are automatically recognized and outputted for indication such as a graded alarm or for the automatic taking of action.

Characteristics or index characteristics may be combined with others. For example, a shape characteristic (which contains the slope data set in the time domain) may be combined with a frequency characteristic to provide a time series of a mathematical index of the slopes and the frequencies of the composite objects which can be ordered in an object hierarchy of ascending object data sets and correlated with other object level of other object data sets The next level, termed the "global objects level" is then derived from the time series of complex objects. At this level global characteristics are derived from the time series datasets of complex objects (and all of their characteristics). At the global objects level, the processor can identify general specific patterns over many hours of time. An example of one specific pattern which is readily recognizable at this level would be a pattern of regular monotonous occurrence of negative reciprocations alternating with positive reciprocations at the complex level comprised of composite objects, wherein the composite objects are derived of regular reciprocations of negative reciprocations alternating with positive reciprocations (of tidal breathing) at the composite level and wherein the magnitude of both the negative and positive reciprocations at the composite level oscillates in a regular frequency. This pattern is typical of Cheyenne-Stokes Respirations and according to the present invention an expert system examines the pattern of the objects at the composite level, the complex level, and finally at the global level to provide distinction between this process and the patterns of upper airway instability.

Additional higher levels can be provided if desired as by a "comprehensive objects level" (not shown), which can, for example, include multiple overnight, or post operative monitoring periods wherein a comprehensive object is comprised of a dataset of "global objects".

While FIG. 2 illustrates the levels of object derivations of a ventilation signal, in another example a similar hierarchical architecture can be derived for the timed data set of the pulse waveform (as from an arterial pressure monitor or the plethesmographic pulse) or any of the parameters discussed below. For the plethesmographic pulse the fundamental level is provided by the pulse tracing itself and includes all the characteristics such as ascending and descending slope, amplitude, frequency, etc. This signal also includes the characteristic of pulse area (which, if applied to a precise signal such as the flow plot through the descending aorta, is analogous to tidal volume in the fundamental minute ventilation plot). When the pulse signal is plethesmographic, it is analogous to a less precise signal of ventilation such as nasal pressure or thermister derived airflow. With these less precise measurements, because the absolute values are not reliable indicators of cardiac output or minute ventilation, the complex spatial relationships along and between signals become more important than any absolute value of components of the signal (such as absolute amplitude of the ascending pulse or inspiration curve). In other word, the mathematical processing of multiple signals that are simply related to physiologic parameters (but are not a true measurement of those parameters) is best achieved by analyzing the complex spatial relationships along and between those signals. To achieve this purpose, according to the present invention, as with ventilation, the pulse signal is organized into a similar multi-level hierarchy of overlapping time series of objects. Subsequently these are combined and compared with the processed objects of respiration. The relationships between a plurality of streaming data sets of the ascending objects of FIG. 2 are conceptually represented in FIG. 4 (discussed below) which can include a hierarchy of time series of streaming objects indicative of a timed drug infusion. A time series of such infusion can include, for example, reciprocations derived from bolus infusions superimposed on a baseline (as with a patient controlled analgesia pump). Here, as discussed, all the time series (included those of the drug infusion) can be ordered into ascending hierarchy and correlated with each of the different levels of other time series.

Figure 3A:
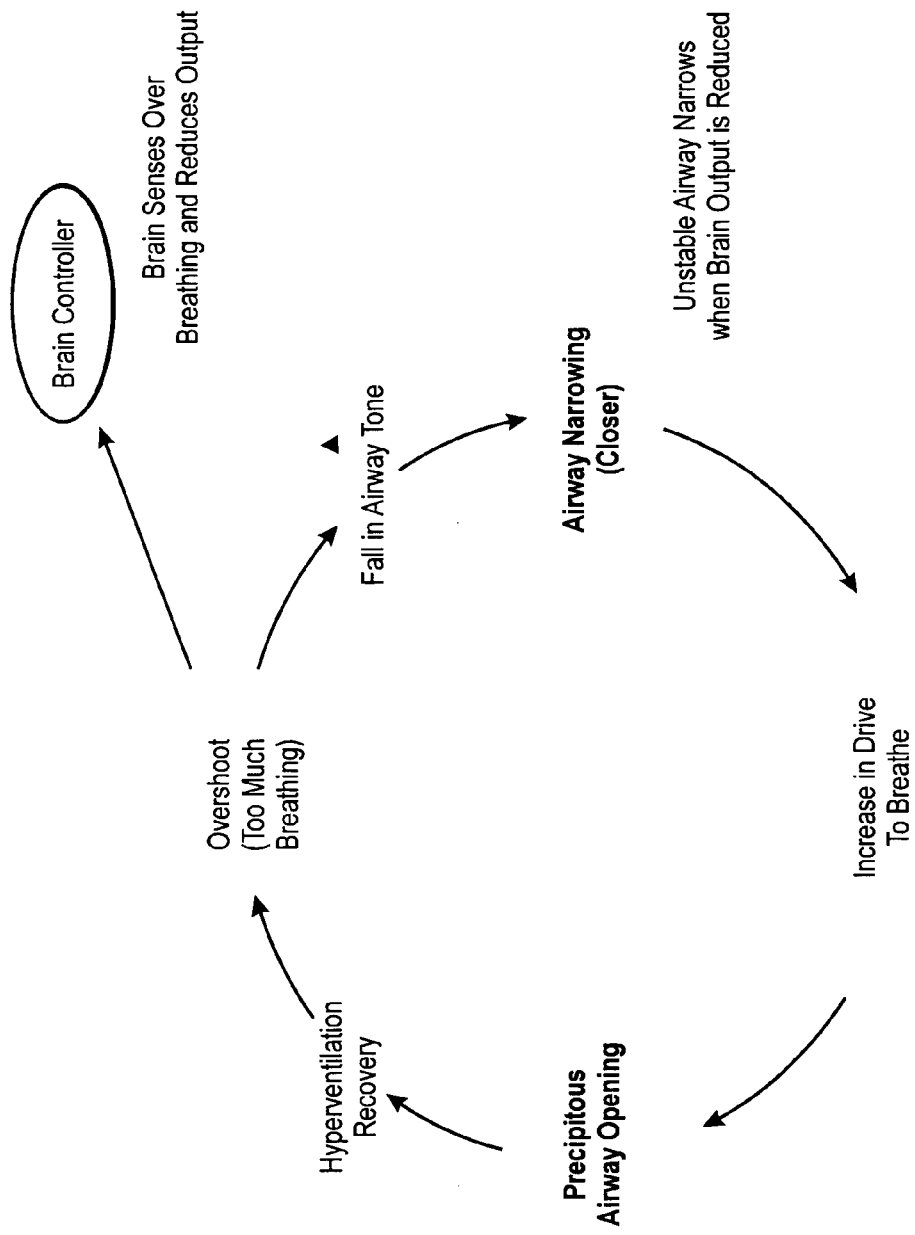
FIG. 3a shows an illustration of the complexity of the mechanisms defining the timed interactions of physiologic systems induced by upper airway instability, which the present inventor calls an "airway instability cluster reentry cycle" showing the derivative reciprocations, which are generated by the cycling producing the corresponding cluster of reciprocations.
Figure 3B:
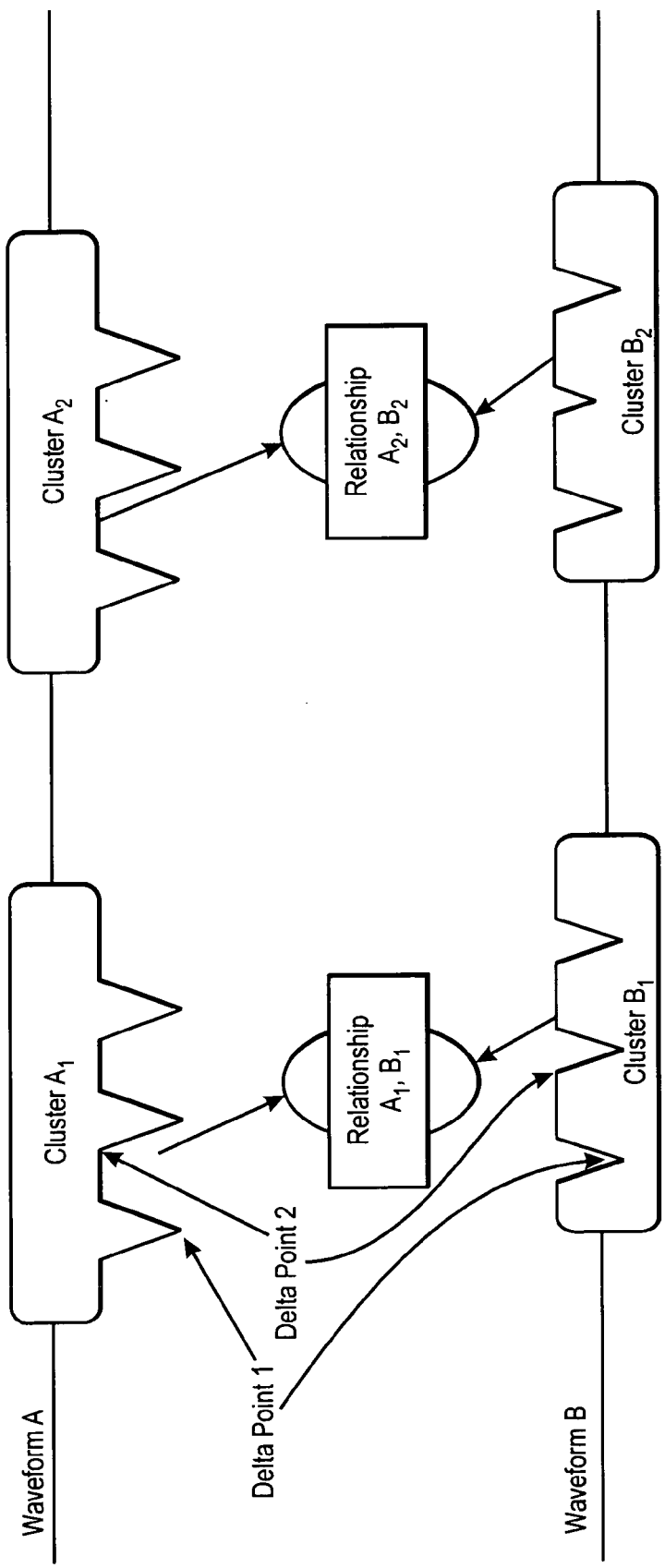
FIG. 3b shows a schematic object mapping at the composite level of two simultaneously measured parameters, which are perturbed to produce clusters in response to the upper airway instability cycles of FIG. 3a, which is automatically detected according to the present invention.
Figure 3C:
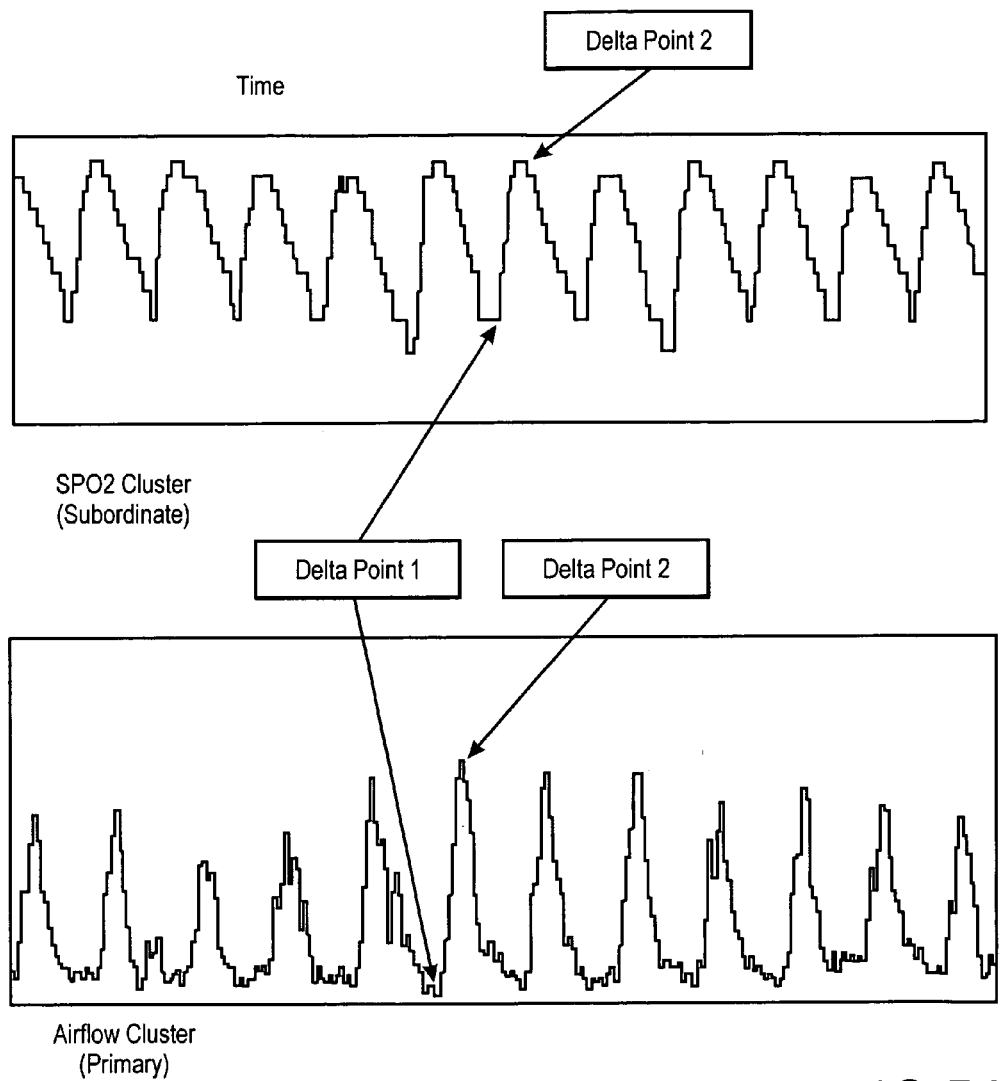
FIG. 3c shows an example of a monomorphic cluster pattern indicative of airway instability and derived from the mechanism of FIG. 3a, which is automatically detected according to the present invention. The figure shows a raw data set of pulse rate (by oximetry), airflow (by nasal-oral thermister).
Figure 3D:
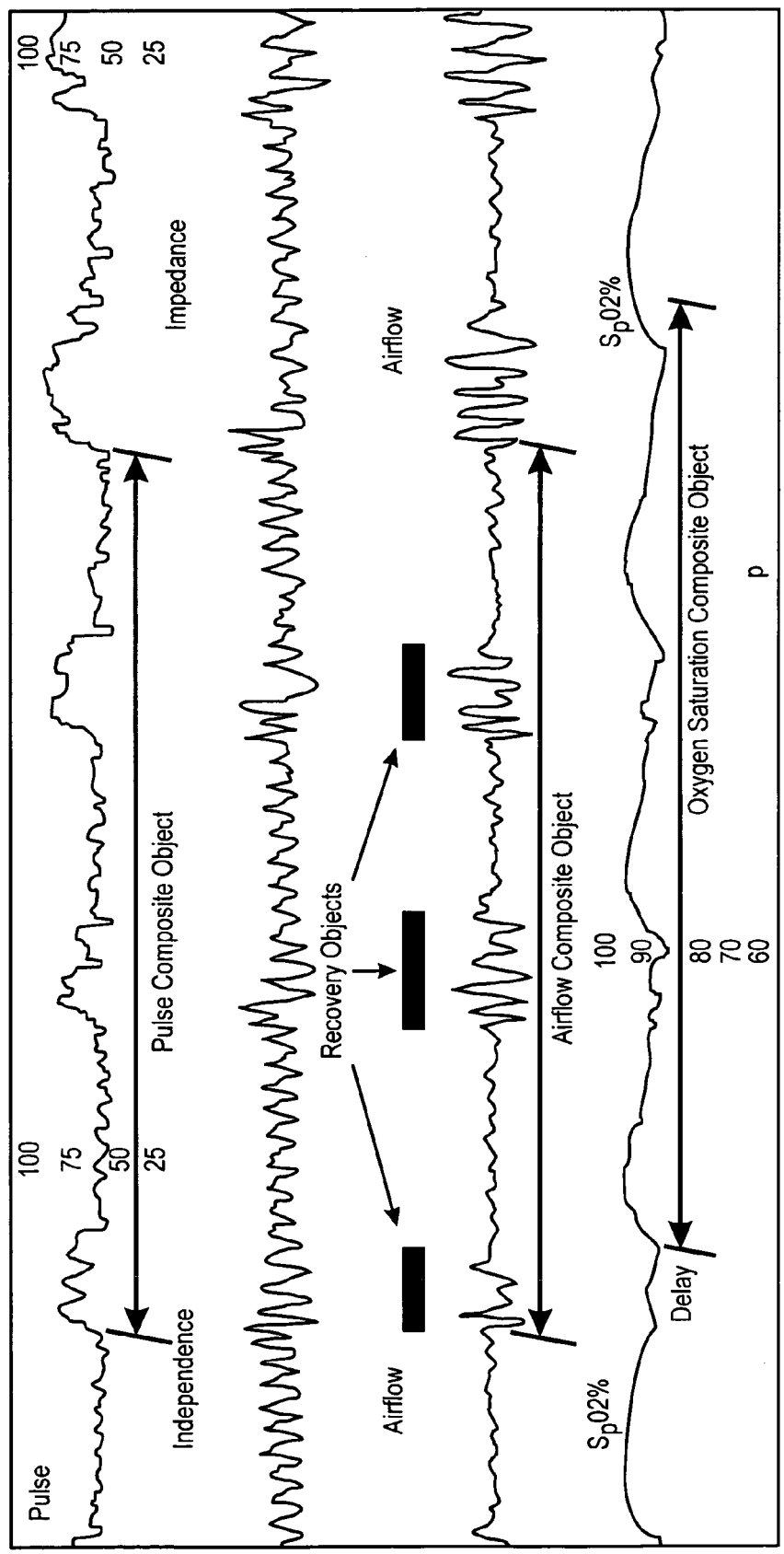
FIG. 3d shows another example of monomorphic cluster pattern derived from the mechanism of FIG. 3a, which now includes a corresponding pulse rate cluster, which is automatically detected according to the present invention. Note the fundamental airflow positive and negative reciprocations in this figure generate larger scale positive reciprocations of airflow recovery (with the patterns shown in FIG. 3b)

FIG. 3a shows an exemplary pathophysiologic process associated with a characteristic dynamic pattern of interaction. As discussed previously, this cyclic process is induced by upper airway instability producing derivative reciprocations across a wide range of physiologic parameters. FIG. 3b shows a schematic object mapping at the composite level of two simultaneously measured parameters which are perturbed to produce clusters in response to the upper airway instability cycles of FIG. 3a, this schematic demonstrates the basic cluster pattern of timed plots, the schematic shows the airway instability clusters as negative reciprocations but according to the present invention they can also be recognized as positive oscillations these can also be recognized as positive reciprocations. According to the present invention, upper airway instability and/or ventilation instability is detected by recognizing these cluster patterns along one or more of the timed plots of: EEG frequency and/or amplitude, chest and/or abdomen movement (by impedance, strain gauge or other method), pulse rate and or RR interval (by oximetry, and/or EKG or other method), pulse amplitude and/or pulse transit time, EMG, oxygen saturation (by pulse oximetry, and/or intravascular venous or arterial oximetry), continuous blood pressure, exhaled carbon dioxide, nasal flow and/or pressure (as by thermister and/or pressure monitoring, or other method), minute ventilation measurements (as by pneumotachometer or other method), snoring (as by pressure monitoring and/or microphone or other method), airway impedance (as by oscillation or other method), FIGS. 3c, and 10a show examples of a monomorphic cluster pattern indicative of airway instability and derived from the mechanism of FIG. 3a, the patterns of which are automatically detected according to the present invention. FIG. 3c shows a raw data set of pulse rate (by oximetry), airflow (by nasal-oral thermister). Another example is shown in FIG. 3d, which now includes a corresponding pulse rate cluster, which is automatically detected according to the present invention. Note the fundamental airflow positive and negative reciprocations in this figure generate larger scale positive reciprocations of airflow recovery (with the patterns shown in FIG. 3c)

Figure 3E:
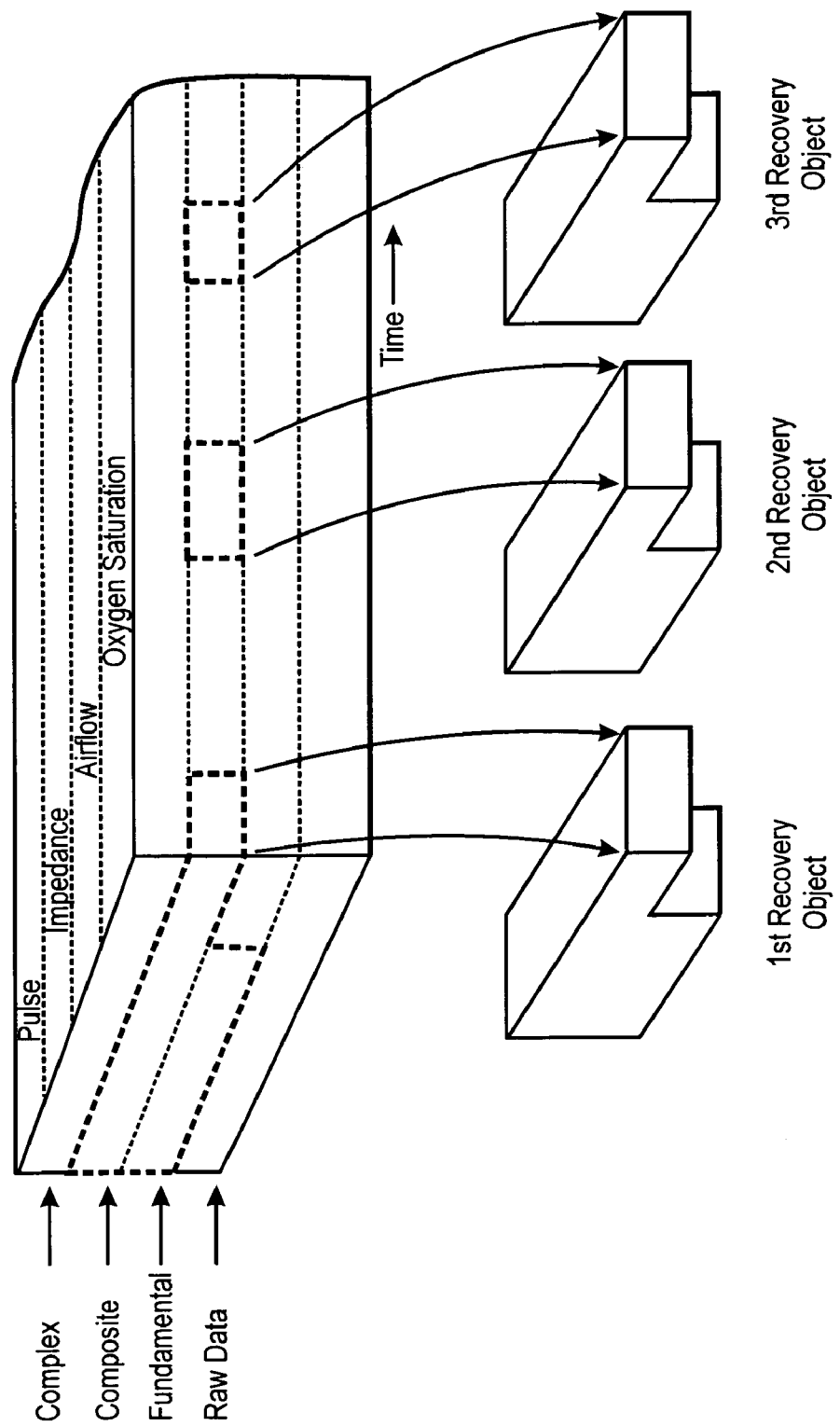
FIG. 3e shows a schematic representation of a portion of a multi-signal object as derived from the multiple corresponding time series of FIG. 3c with three multi-signal recovery objects at the composite object level identified for additional processing according to the present invention. Note that objects at the composite level encapsulate the waveform objects from lower levels.

In the presently preferred embodiment, the time series of each of these signals are processed into time domain fragments (as objects) and organized into the object levels as previously discussed. For the purpose of organizing and analyzing complex interactions between these corresponding and/or simultaneously derived signals, the same basic ascending process is applied to each signal. As shown in FIG. 3e these streaming objects, many of which overlap, can be seen to conceptually project along a three-dimensional time series comprised of multiple levels of a plurality of corresponding signals. A "multi-signal object" is comprised of at least one object from a first signal and at least one object from another signal.

This type of representation is too complex for presentation to hospital personnel but is preferred for the purpose of general representation of the data organization because, at this level of complexity, a complete representation of multiple time series does not lend itself well to a two-dimensional graphical (and in some cases a three dimensional) representation.

To illustrate the complexity ordered by this approach, consider the components of just one of the three simple recovery objects shown in FIGS. 3c and 3e. This single recovery object includes the following exemplary characteristics, each of which may have clinical relevance when considered in relation to the timing and characteristics of other objects;

1. Amplitude, slope, and shape of the oxygen saturation rise event at the composite level.
2. Amplitude, slope, and shape of the ventilation rise event at the composite level which contains the following characteristics at the fundamental level;
   Amplitude, slope, time and shape of the inspiration rise object
   Amplitude, slope, time and shape of the expiration fall object.
   Frequency and slope dataset of the breath to breath interval of reciprocations (tidal breathing) objects
3. Amplitude, slope, and shape of the pulse rise event at the composite level which contains the following exemplary characteristics at the fundamental level;
   Amplitude, slope, and shape of the plethesmographic pulse rise event.
   Amplitude, slope, and shape of the plethesmographic pulse fall event.
   Frequency and slope datasets of beat-to-beat interval of the pulse rate.

As is readily apparent, it is not possible for a health care worker to timely evaluate the values or relationships of even a modest fraction of these parameters and an expert system applied generally to these parameters rapidly becomes inordinately complex and cumbersome. For this reason the output based on the analysis of these time series of objects are optimally first ordered into a relational, inheritance based object hierarchy, and then subjected to expert system analysis and/or presented in a succinct and interpretive format to the hospital worker as will be discussed.

FIG. 4 provides a conceptual representation of one presently preferred relational data structure of multiple time series, according to the present invention. This representation shows that the many time series of objects are organized into different corresponding streams of objects, which can be conceptually represented as a cylindrical matrix 1, with time defining the axis along the length of the cylinder 1. In this example the cylinder 1 is comprised of the four streams of objects each stream having three levels and these are matched and stored together in a relational database, object database or object-relational database. Each streaming set of objects from a single signal or source (e.g. airflow or oximetry, as in a matrix of physiologic signals) is represented in the main cylinder 1 by a smaller cylinder (2,3,4,5) and each of these smaller cylinders is comprised of a grouping of ascending object levels (6,7) as will be described. One important advantage of organizing the data in this way is that each object from each grouping can be readily compared and matched to other objects along the grouping and can further be compared and matched to other object from each other grouping. Objects occurring at one time in one level encapsulate the objects at lower levels so that objects of a first grouping can be readily compared to objects occurring at another time and at another level of at least one other grouping. Complex patterns and subtle relationships between interactive and interdependent streams of objects can be readily defined by applying an expert system or by manually or automatically searching the matched object streams as will be discussed. This allows for the recognition of the "Dynamic Pattern of Interaction" (DPI) between data set objects. The recognition of a specific DPI occurrence falling within a specified range is used to determine the presence and severity of a specific of a biologic or physical process.

One of the longstanding problems associated with the comparison of outputs of multiple sensors to derive simultaneous multiple time series outputs for the detection of pathophysiologic change is that the accuracy and/or output of each sensor may be affected by different physiologic mechanisms in different ways. Because of this, the value of matching an absolute value of one measurement to an absolute value of another measurement is degraded. This is particularly true if the measurement technique or either of the values is imprecise. For example, when minute ventilation is measured by a precise method such as a pneumotachometer, then the relationship between the absolute values of the minute ventilation and the oxygen saturation are particularly relevant. However, if minute ventilation is being trended as by nasal thermister or nasal pressure monitoring or by chest wall impedance, then the absolute values become much less useful. However, according to one aspect of the present invention the relationship between pluralities of simultaneously derived signals can be determined independent of the relationships of the absolute values of the signals. In this way, simultaneously derived signals can be identified as having convergence consistent with physiologic subordination or divergent shapes consistent with the development of a pathologic relationship or inaccurate data acquisition.

As noted, with physiologically linked signals, a specific occurrence or magnitude of change in one signal in relationship to such a change in another signal may be more important and much more reproducible than the absolute value relationships of the respective signals. Using the teachings of the present invention, two simultaneously acquired and physiologically linked signals are compared by the microprocessor over corresponding intervals by matching the respective objects (which can be applied at multiple levels) between the signals. As discussed, a primary signal such as airflow is ordered into composite and complex objects along with a contemporaneously measured secondary signal such as oxygen saturation as by the method and system discussed previously. For example, the composite level of airflow can be a of reciprocation objects derived from a fundamental level of amplitude and/or frequency of the tidal airflow as by thermister or pressure sensor, or another plot, which is indicative of the general magnitude of the timed tidal airflow. In the presently preferred embodiment, a plot at the fundamental level of a mathematical index (such as the product) of the frequency and amplitude is preferred, because such an index takes into account the important attenuation of both amplitude and frequency during obstructive breathing. Furthermore, both the frequency and amplitude are often markedly increased during the recovery interval between apneas and hypopneas.

Figure 6:
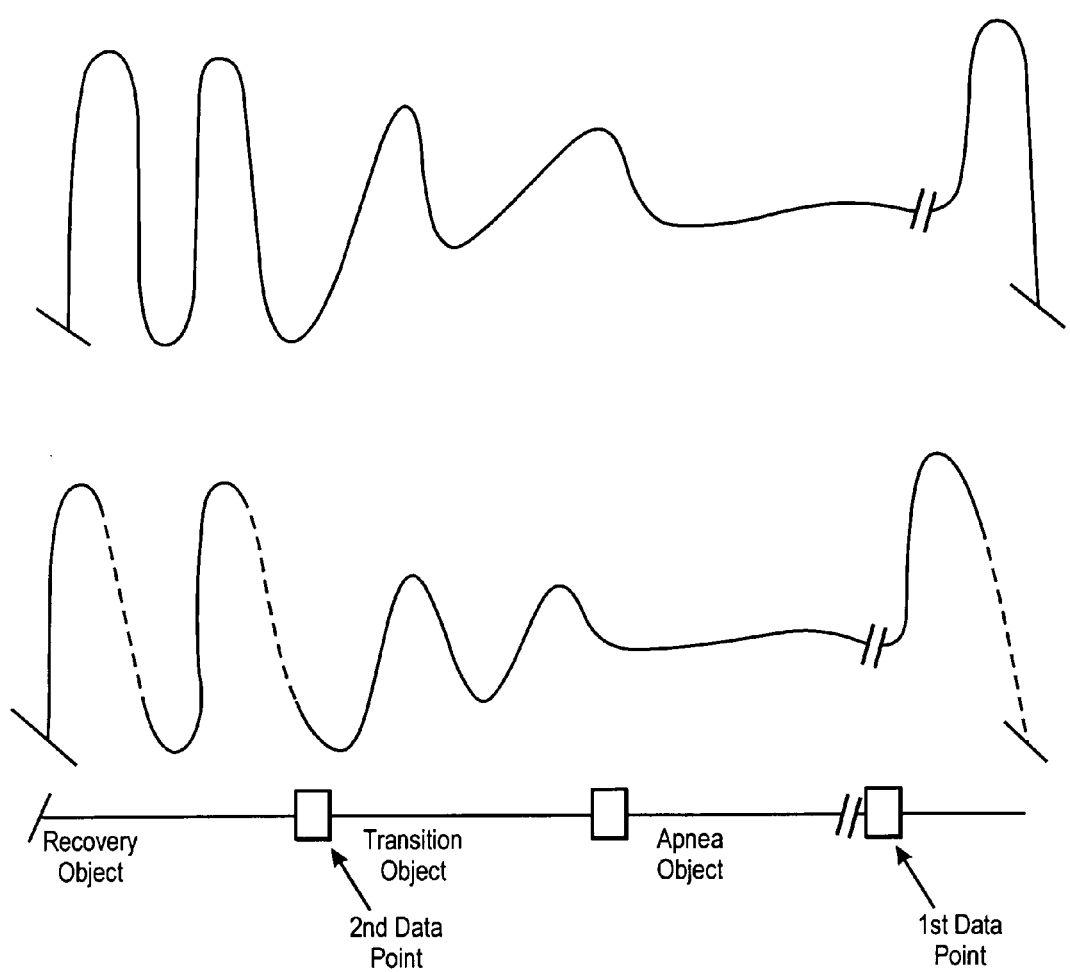
FIG. 6 shows a comparison between two data sets of tidal airflow reciprocations at the fundamental level wherein the second data set shows evidence of expiratory airflow delay during the recovery object, note that the recovery object is recognized at the composite level and it has inherited (and therefore encapsulates) the fundamental tidal airflow reciprocation objects.

Although the exact delay between the signals may not be known, the processor can identify this by identifying the best match between the object sets. In the preferred embodiment, this "best match" is constrained by preset limits. For example, with respect to ventilation and oximetry, a preset limit could be provided in the range of 10–40 seconds although other limits could be used depending on the hardware, probe site and averaging intervals chosen. After the best match is identified, the relationships between the signals are compared (for example, the processor can compare the a rise or fall event of oxygen saturation to a rise or fall event of ventilation as shown in FIG. 6). In this preferred embodiment, each such event is compared. It is considered preferable that the objects of each respective parameter relate to a similar duration. With respect to airflow, calculation of the magnitude value of airflow may require sampling at a frequency of 25 hertz or higher, however, the sampling frequency of the secondary plot of the magnitude value of the index can, for example, be averaged in a range of one hertz to match the averaging interval of the data set of oxygen saturation.

It is not necessary that such a fundamental level plot reflect exactly the true value of the minute ventilation but rather, it is important that the plot reflect the degree of change of a given level of minute ventilation. Since these two signals are physiologically linked, an abrupt change in the primary signal (airflow) generally will produce readily identifiable change in the subordinate signal (oxygen saturation). As previously noted, since the events which are associated with airway collapse are precipitous, the onset of these precipitous events represent a brief period of rapid change which allows for optimal detection of the linkage between the primary signal and the subordinate signal.

Figure 5:
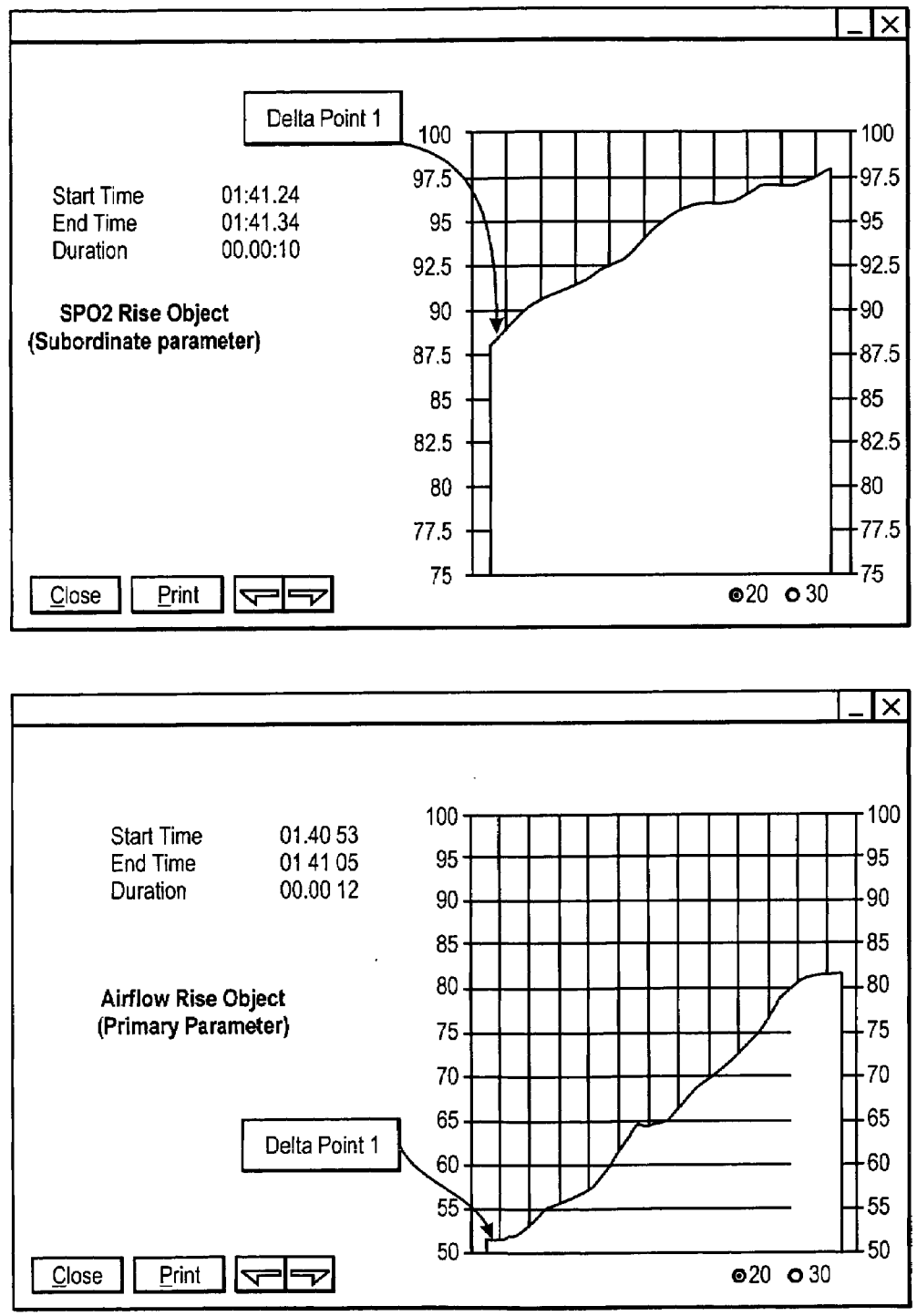
FIG. 5 shows a selected subordinate composite object of oxygen saturation of FIG. 3c, matched with its corresponding primary composite object of airflow, as they are stored as objects at the composite level in the relational database, object database or object-relational database.

The signals can be time matched by dipole slopes at the fundamental level. In addition, in one preferred embodiment, the point of onset of precipitous change is identified at the composite object level of the primary signal and this is linked to a corresponding point of a precipitous change in the composite object level of the subordinate signal. This is referred to herein as a delta point. As shown in FIGS. 3c, 5, and 6, a first delta point is identified in the primary signal and in this example is defined by the onset of a rise object. A corresponding first delta point is identified in the subordinate signal and this corresponds to the onset of a rise object in the subordinate signal. A second delta point is identified which is defined by the point of onset of a fall object in the primary signal and which corresponds to a second delta point in the subordinate signal defined by the onset of a fall event in the secondary signal. The point preceding the second delta point (the "hyperventilation reference point") is considered a reference indicating an output associated with a degree of ventilation, which substantially exceeds normal ventilation and normally is at least twice normal ventilation. When applying airflow as the primary signal and oximetry as the subordinate signal, the first delta point match is the most precise point match along the two integrated waveforms and therefore comprises a ("timing reference point") for optimally adjusting for any delay between the corresponding objects of the two or more signals. The mathematical aggregate (such as the mean) of an index of the duration and slope, and/or frequencies of composite rise and fall objects of the fundamental level of tidal ventilation along a short region adjacent these reference points can be applied as a general reference for comparison to define the presence of relative levels of ventilation within objects along other portions of the airflow time series. Important fundamental object characteristics at these reference points are the slope and duration of the rise object or fall object because these are related to volume of air, which was moved during the tidal breath. The fundamental objects comprising the tidal breaths at the reference hyperventilation point along the composite level are expected to have a high slope (absolute value) and a high frequency. In this way both high and low reference ranges are determined for the signal. In another preferred embodiment, these points can be used to identify the spatial shape configuration of the rise and fall objects at the fundamental level during the rise and fall objects at the composite level.

Using one presently preferred method, a first object (such as is shown in FIG. 5) can then identified in the primary signal (such as, for example, airflow) at the composite object level between the first delta point and the second delta point which is designated a recovery object. As also shown in FIG. 5 the matched recovery object (for example oxygen saturation) is also identified in the subordinate signal as the point of onset of the rise object to the point of the onset of the next subsequent fall object. In the preferred embodiment, the recovery object is preceded by the apnea/hypopnea object which is defined by the point of onset of the fall object to the point of onset of the next rise object in both the primary and subordinate signals.

Once the signals have been sufficiently matched at the one object level they can be further matched at another object level. When the objects are matched, the baseline dynamic range relationship between the signals can be determined. This baseline range relationship can be a magnitude value relationship or a slope relationship. The signals can then be monitored for variance from this baseline range, which can indicate pathology or signal inaccuracy. The variance from baseline can be, for example, an increase in the relative value of ventilation in relation to the oximetry value or a greater rate of fall in oxygen saturation in relation to the duration and/or slope of fall of ventilation. In another example, the variance can include a change from the baseline delay between delta points along the signals or a change in the direction (polarity) of one signal in relation to the baseline relationship for example two signals which formally moved in the same direction (after adjusting for a delay) may be recognized to exhibit variance by moving in opposite directions and the occurrence of this variance from a previously identified dynamic relationship (or a pre specified dynamic relationship range) Upon such recognition, according to the present inventor, the processor can be programmed to take action such as lock out a medication, adjust the flow of oxygen, change the positive pressure or tidal volume of a ventilator, or provide an indication, such as an alarm.

Figure 7:
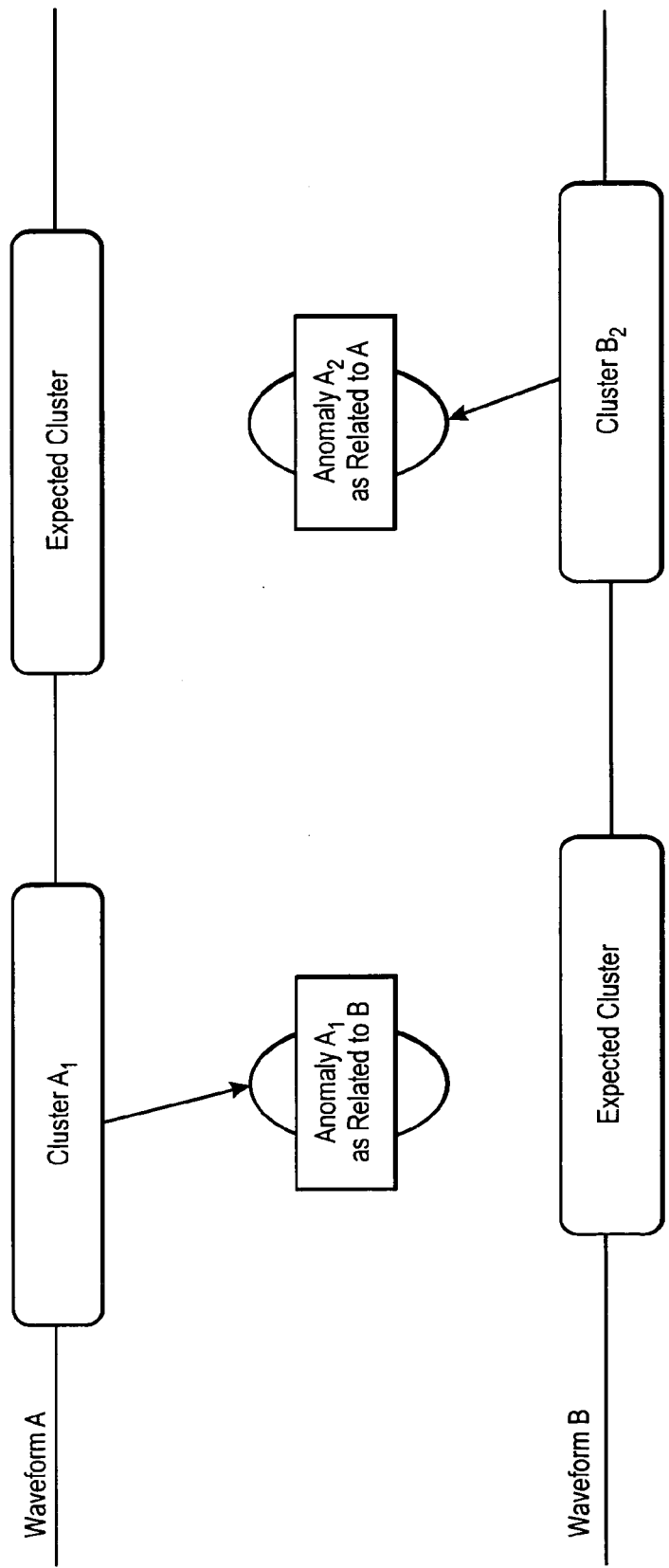
FIG. 7 shows a schematic object mapping at the composite level of two simultaneously measured parameters with a region of anticipated composite objects according to the present invention.
Figure 8:
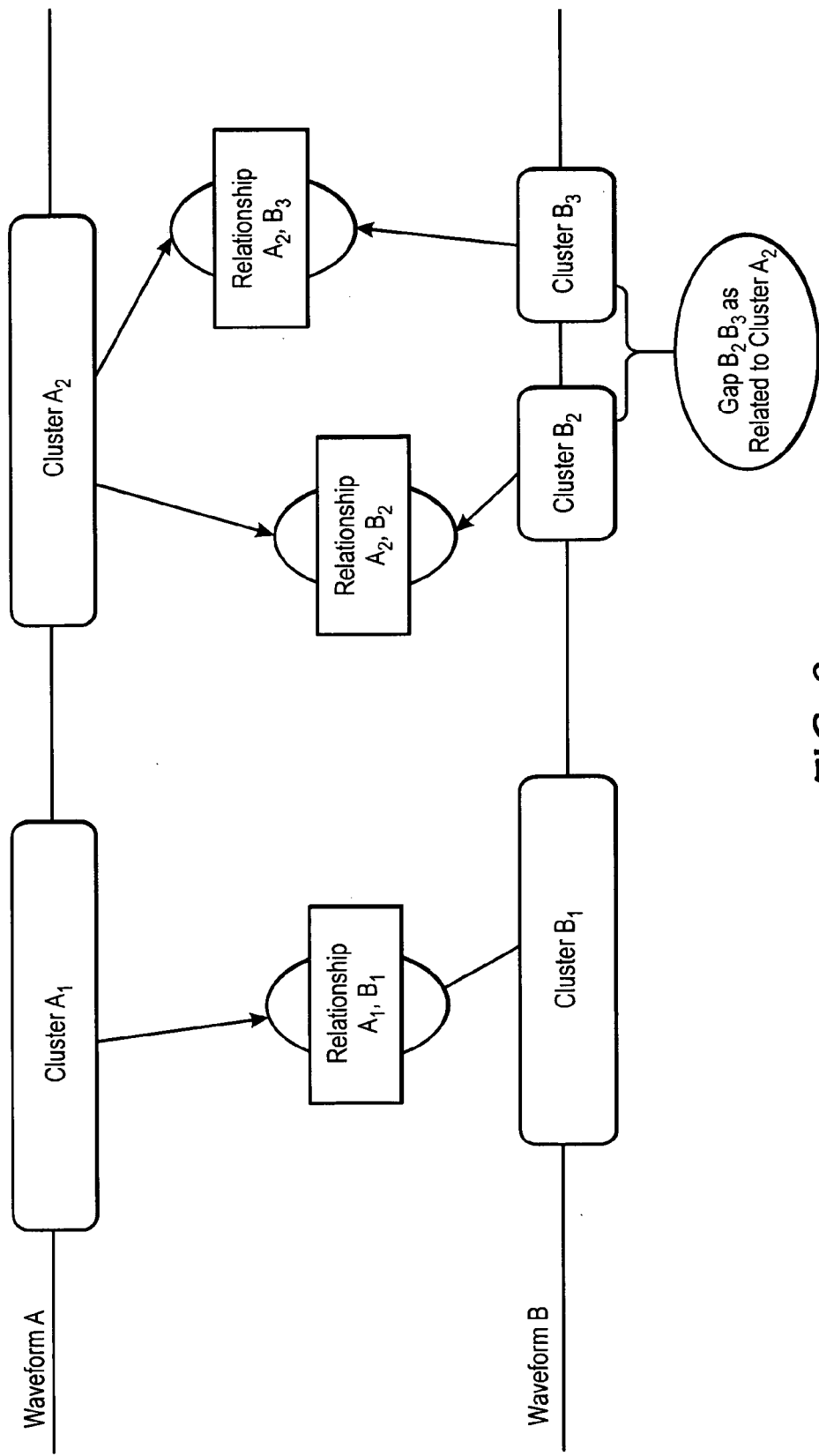
FIG. 8 shows a schematic object mapping and scoring at the composite level of two simultaneously measured parameters with the region of anticipated composite objects according to the present invention.
Figure 9:
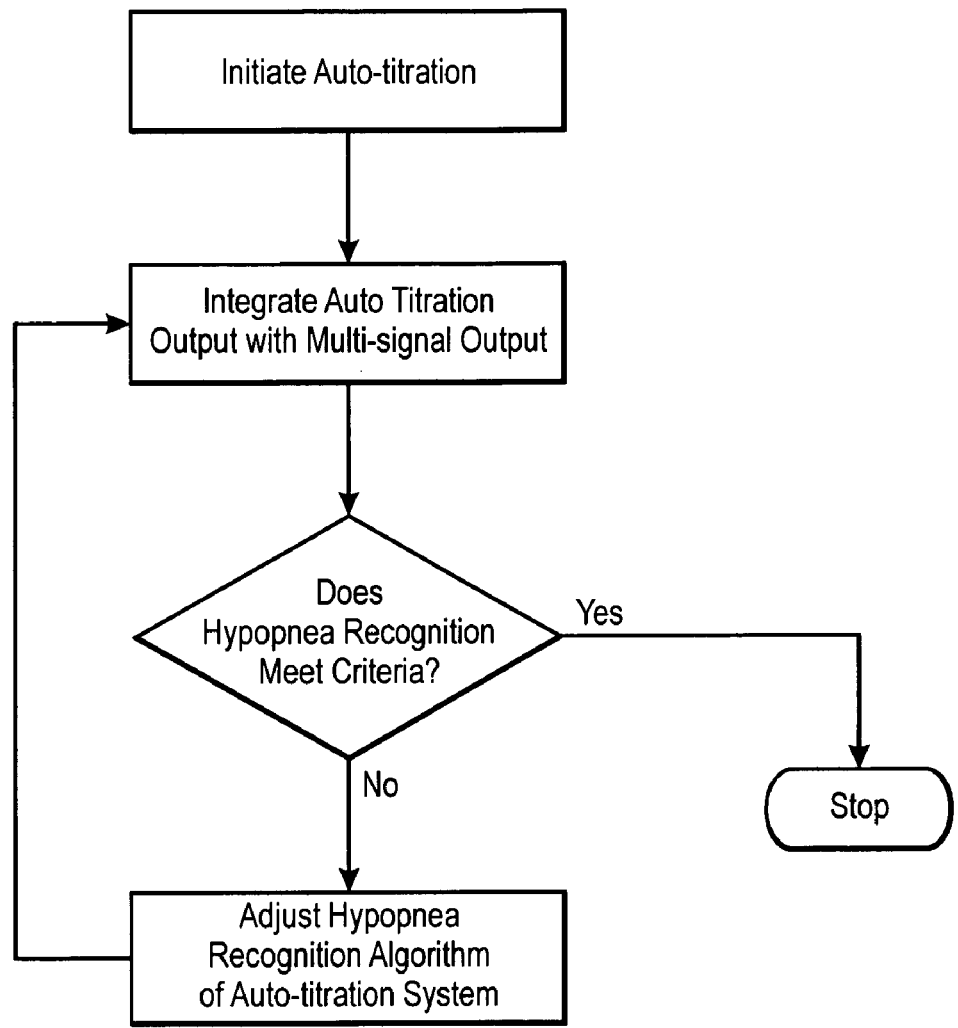
FIG. 9 shows a schematic of a system for customizing a CPAP auto-titration algorithm based on the analysis of reciprocations of multiple corresponding signals across multiple scales.

According to the present invention, clusters of signal perturbation induced by even mild hypopneas can generally be reliably recognized by their cluster patterns utilizing with only a single parameter without setting up a priori and arbitrary rules (such as a 50% reduction in the airflow signal). In addition, when significant signal noise or reduced gain is present reducing cluster recognition in one signal, the objects based system can combine matched clusters within a time series of multi-signal objects in the presence of sub optimal signals by providing a scoring system for sequential objects across a wide range of parameters. FIGS. 7, and 8 show schematics of the basic cluster matching for two parameters in situations wherein sub optimal signals may be present although many more parameters may be combined in this way. In one example, the matched clusters can be paired timed datasets of airflow and oximetry include a matched sequence of negative reciprocations in the airflow signal and corresponding delayed negative reciprocation in the oximetry signal. One exemplary method of achieving match with an incomplete set of matching objects in one of the signals follows; Each reciprocation at the composite level is defined by a set of coupled rise and fall objects meeting criteria and occurring within a predetermined interval of each other (as discussed previously). The occurrence of reciprocation in either dataset meeting all criteria is given a score of 1.

The reciprocations are counted in sequence for each matched cluster object. For the purpose of illustration, according to the present invention, the occurrence of a score of 3 in any one signal (meaning that a continuous sequence of 3 reciprocations meeting criteria have occurred within a specified interval) provides sufficient evidence to identify a cluster object. When two simultaneous signals are processed, a total score of 4, derived from adding the number of reciprocations meeting criteria in each signal, is sufficient to indicate the presence of a cluster object. In this manner the cluster is continued by a sequential unbroken count greater than 3 with one signal, or greater than 4 with two signals. Once the presence of a cluster object has been established along the time series, at any point along the cluster object the sequential count along one signal can be converted to a continuation of the sequential count along another signal allowing the cluster object to continue unbroken. The failure of the occurrence of a cycle meeting criteria within either signal within a specified interval (for example about 90–120 seconds, although other intervals may be used) breaks the cluster object. A new cluster object is again identified if the count again reaches the thresholds as noted above. It can be seen that this scoring method takes into account the fact that artifact often affects one signal and not another. Therefore if either signal alone provides a sufficient score, the presence of a cluster object is established. In addition, the effect of brief episodes of artifact affecting both signals is reduced by this scoring method. In this way, artifact, unless prolonged, may cause the cluster object to be broken but as soon as the artifact has reduced sufficiently in any one or more signals the process of scoring for a new cluster object will restart. The skilled artisan will recognize that many other such scoring or artifact rejecting methods using two linked signals can be derived within the scope of this teaching.

When applied, one preferred digital pattern recognition program for automatically detecting, characterizing and indexing the severity airway instability proceeds in several phases, which need not be in the illustrative sequence, listed below:

1. Various types of decline and rise objects are identified at the composite level.
2. Various types of negative and positive reciprocations are identified at the composite level.
3. Various types of clusters of reciprocations are identified in the complex level.
4. Various types of reciprocations of clustered reciprocation object characteristics (e.g. nadirs) are identified,
6. Reciprocations at the fundamental level are analyzed within specific objects at the composite level.
7. Objects of one channel are compared to objects of another channel (if multiple time series of objects are rendered).
8. An expert system is applied to recognize a pattern of objects indicative of a diagnosis.
9. The relationship between the events, reciprocations, and complex patterns is calculated and outputted.
10. The severity of the pathophysiologic perturbation is determined
11. A textual alarm and/or other signal, which may be graded based on severity is outputted
12. Treatment is automatically modified to adjust or prevent medication infusion or to eliminate the cluster
13. The process is then repeated with each addition to the dataset in real-time or with stored timed datasets.

A mathematical representation of a basic iterative process of waveform object segmentation according to the present invention is described in detail in the co-pending application entitled System and Method for Identifying Dynamic Patterns of Interaction, the disclosure of which is incorporated by reference as if completely disclosed herein and an exemplary mathematical reference listing is provided in FIGS. 20*a*–20*c*. These basic algorithms are particularly suited to identify monomorphic clusters and which, because of the precipitous nature of the operative pathophysiology driving the airway instability cycle, are largely comprised of two basic types of events (unipolar rise and unipolar fall), and a basic type of reciprocation (a simple negative or positive reciprocation) and a single cluster type (as a collection of negative or positive reciprocations). As will be shown many basic pathophysiologic processes are comprised of this type of simple reciprocations and the basic embodiment suffices to characterizing them.

Figure 10B:
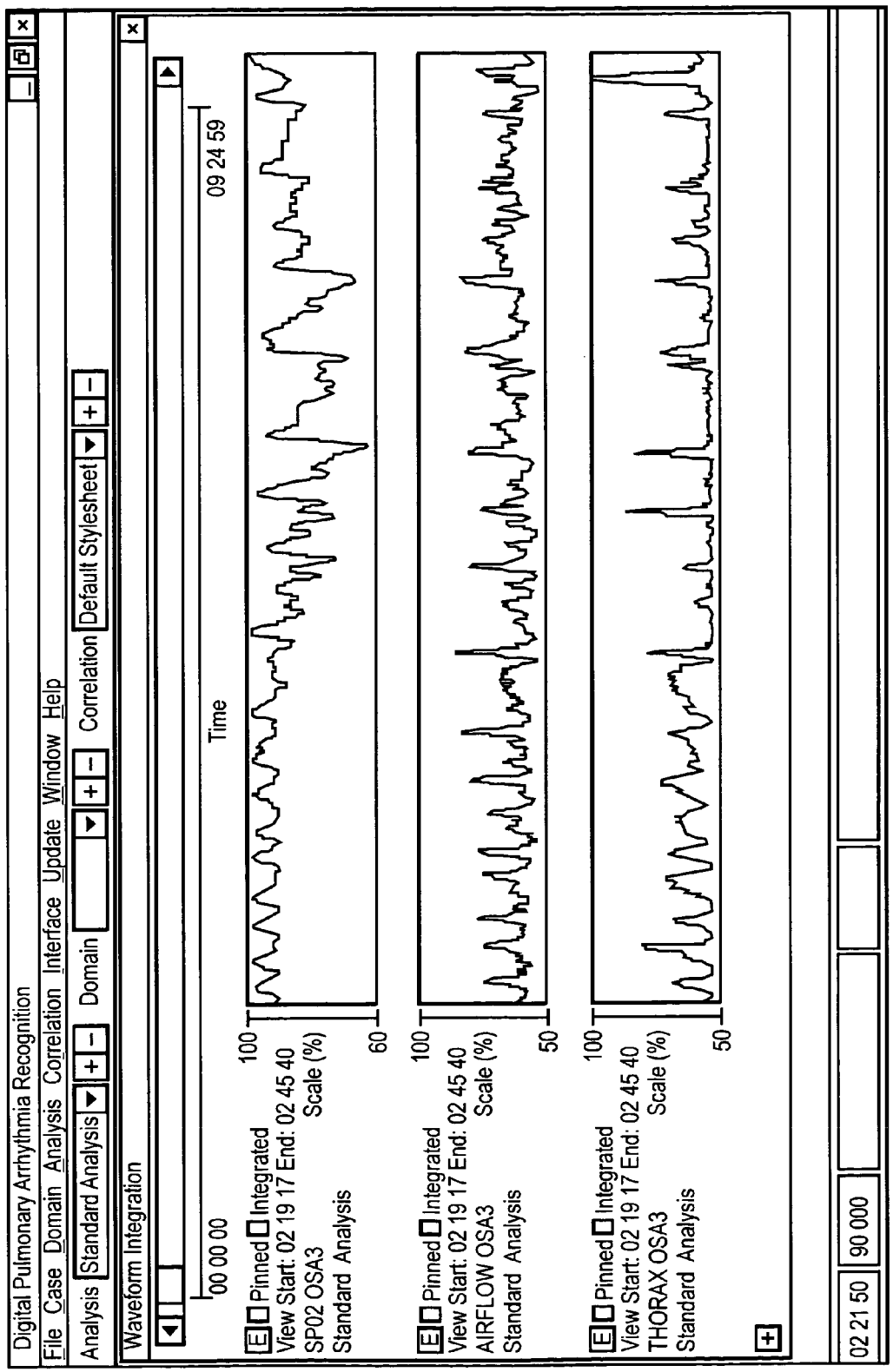
FIG. 10b shows a polymorphic airway instability cluster along times series of oximetry, airflow, and thorax movement
Figure 10C:
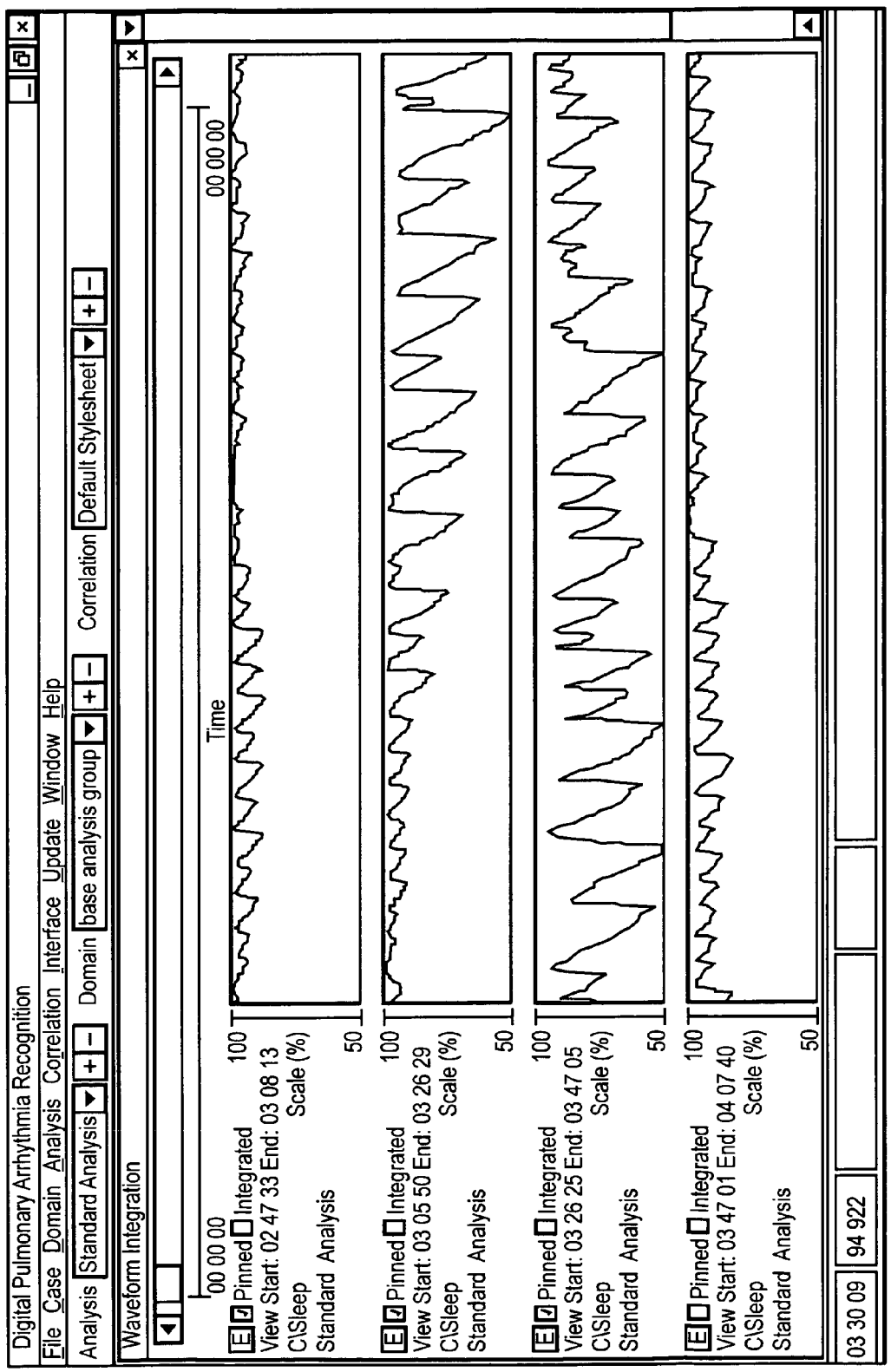
FIG. 10c shows a times series of oximetry over a period of about 2 hours and 40 minutes demonstrating a monomorphic airway instability cluster of negative oxygen saturation reciprocations degenerating into a polymorphic cluster exhibiting marked instability of control evidenced by marked reciprocations of the peaks and nadirs of the negative oximetry reciprocations within the cluster. This represents a markedly adverse pathophysiologic pattern, which is automatically recognized and graded according to the present invention.
Figure 10D:
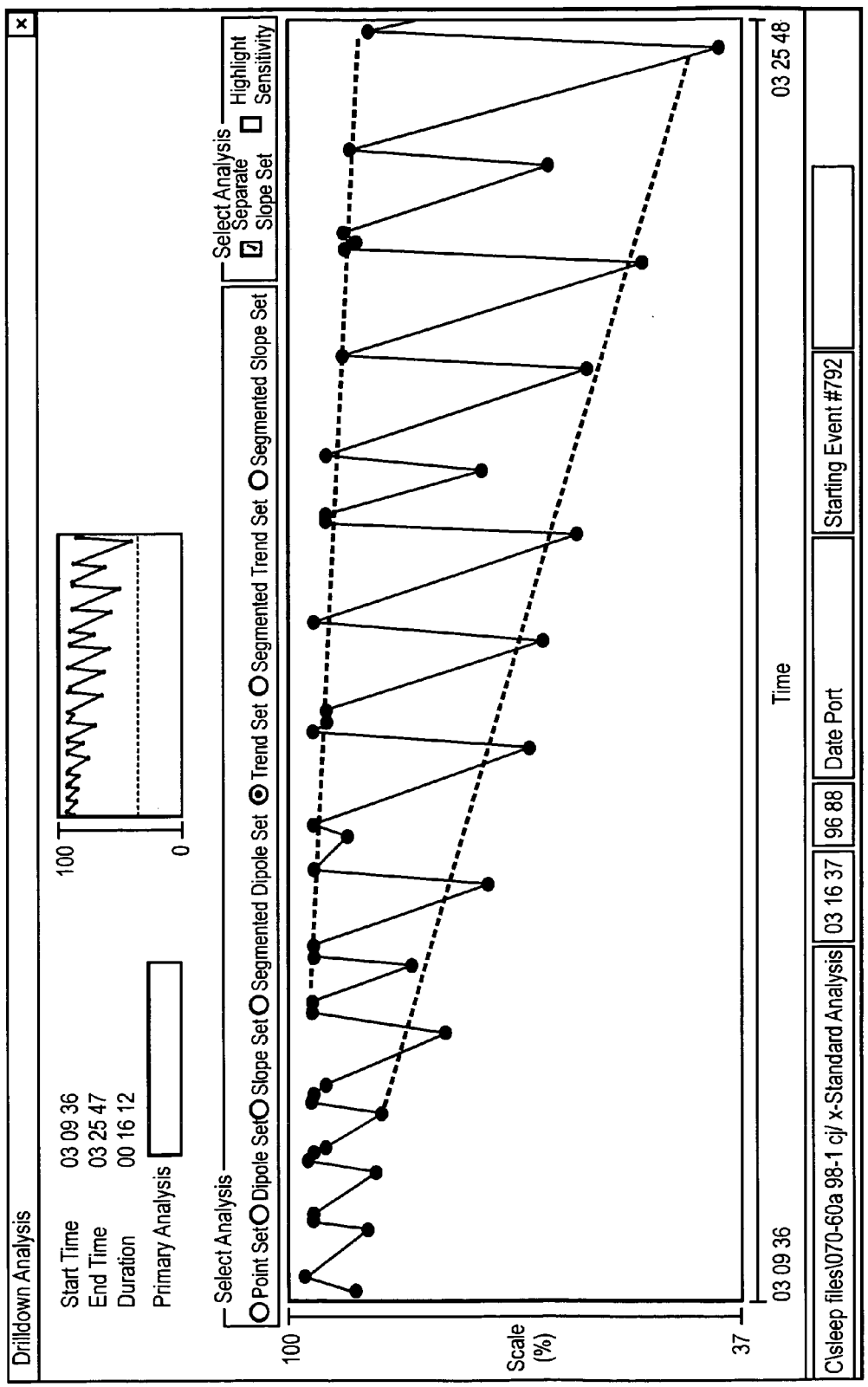
FIG. 10d shows a 16.2-minute segment of the times series of oximetry of FIG. 10d illustrating a modest decline component of a pathophysiologic pattern of monomorphic reciprocation.
Figure 10E:
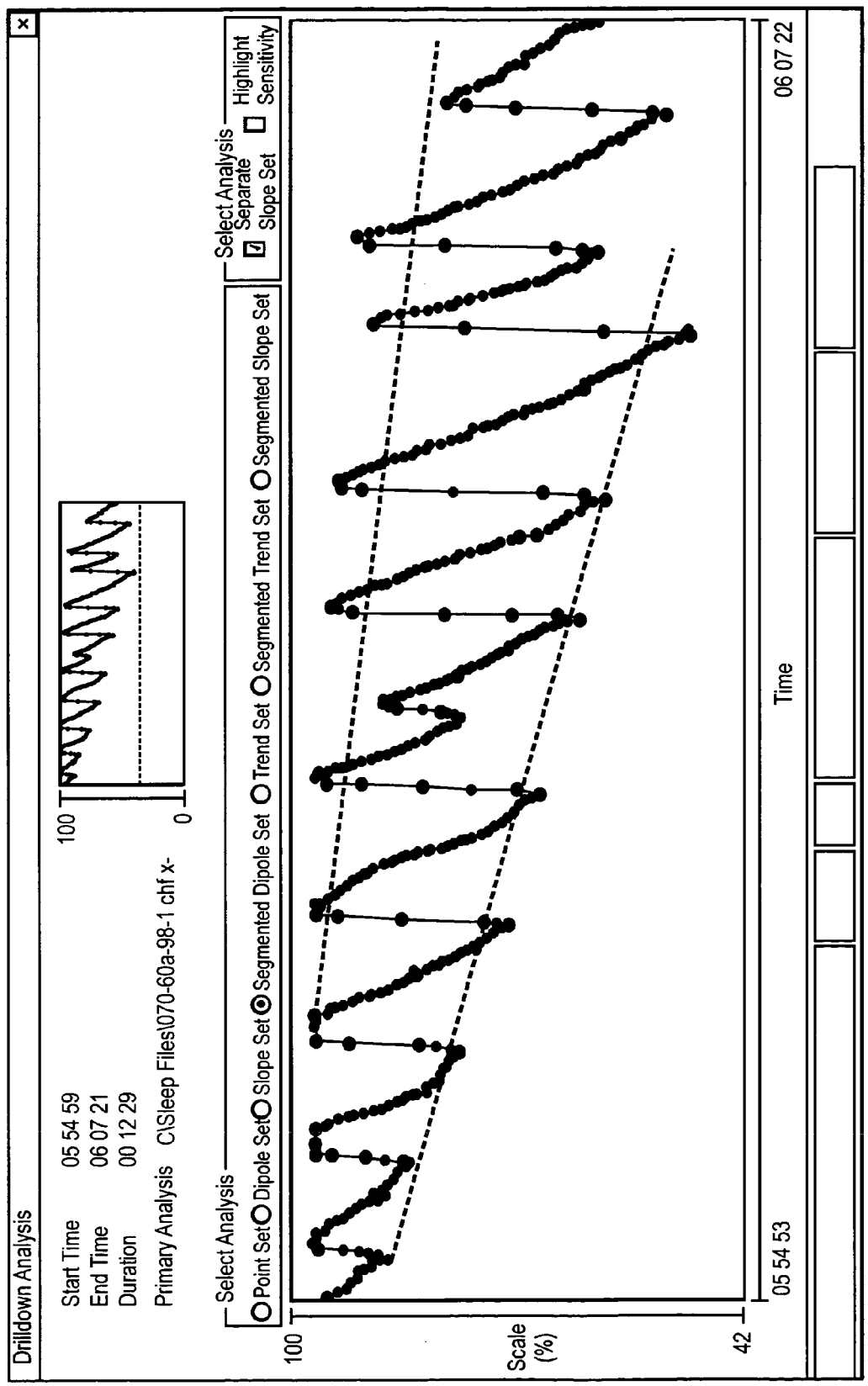
FIG. 10e shows a 12.5-minute segment of a times series of oximetry illustrating a more severe decline of the peaks comprising degeneration into a polymorphic pattern indicative of severely adverse pathophysiologic pattern and which can be indicative of an important decline in arousal threshold and incompletes arousal response which fails to completely correct the negative reciprocation. This polymorphic pattern is automatically recognized according to the present invention to provide an output indication or to take action such as to lock out medication.
Figure 10F:
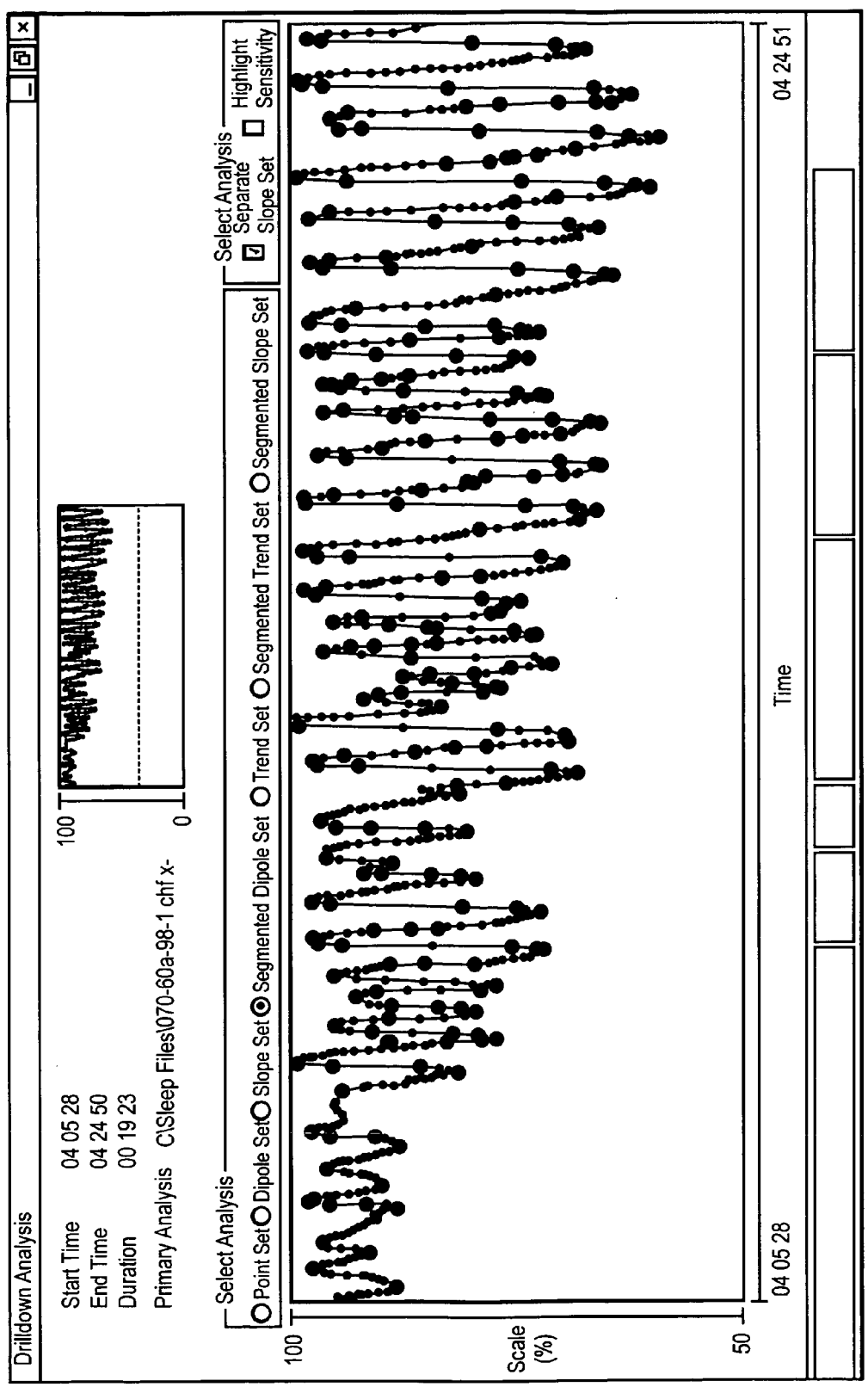

The present inventors have described clusters comprised of reciprocations of varied morphology as polymorphic (an example of such a cluster is shown in FIG. 10b). For the purpose of the presently preferred embodiment, with respect to the oximetry time series, a polymorphic cluster is a cluster of reciprocations, which contains at least two reciprocation morphologies and wherein the morphologies have differences other than simple variations in scale. In one embodiment, with respect to the oximetry time series, variation of the nadirs of the negative reciprocations is considered still consistent with monomorphic clusters. However in this embodiment, naegative reciprocations of the peaks exceeding a 6% variation is considered indicative of a polymorphic cluster. Many modifications and different definitions can be applied to differentiate polymorphic from monomorphic clusters. In one preferred embodiment, the morphology of different reciprocation types is selectable by selecting the characteristics of the events from which they are derived (the reciprocations inheriting these characteristics). A monomorphic cluster may degenerate into a polymorphic cluster, and again this is recognized by identifying the presence of new types of reciprocations or events developing along the cluster. For example the occurrence of brief reciprocations with progressively falling peaks coupled with prolonged reciprocations with prolonged decline components would be one example of morphology of a polymorphic cluster. The present inventors recognized that reciprocation morphology was a window into the integrity and function of the control system. For this reason, the automatic recognition, according to the present invention provides an important function since the presence of a polymorphic cluster can indicate a control system which is highly unstable, severely attenuated, the presence of competing control systems (which can indicate partial attenuation of a primary controller and salvage by a secondary controller, or it can indicate that multiple pathophysiologic process are overlapping).

The present inventors have discover that, at least in one population of patients with airway instability, the basic monomorphic pattern dominates and polymorphic patterns occur in less than 10% of the patients. However, this may increase with narcotic administration or with select subgroups of the severe obesity (at risk for obesity hypoventilation syndrome) or those with COPD, or CHF. The present inventors have discovered that the automatic recognition of complex polymorphic clusters can be useful to determine the stability and integrity of ventilation control and the probability of success of automatic CPAP titration. This is an important discovery because primary care physicians have been reluctant to institute automatic CPAP in the home without attendance because the probability of success for a given patient cannot be known a priori. The present inventors recognized that the presence of polymorphic clusters and/or monomorphic clusters superimposed on other reciprocations (an occurrence which develops, for example, when airway instability is superimposed on other cardiovascular and pulmonary co morbidities) have a lower probability of successful automatic CPAP titration and are therefore may best titrated in a sleep laboratory or other attended setting where a trained attendant can adjust treatment. They also recognized that polymorphic reciprocations are often best treated with multilevel ventilation because they often indicate an incomplete, or delayed recovery, which is often best supported by ventilation rather than simple CPAP.

According to the present invention, a automatic CPAP titration which can use any of a range of algorithms for CPAP adjustment, as are known in the art, upon recognition by the processor of polymorphic clusters, or the presence of a decline in a time series of the peaks of clusters (as for example in the oximetry signal), and/or the failure to abort clusters, the processor is programmed to automatically converts the CPAP to a bi level ventilator. According to the present invention, this can be achieved by automatically lowering the pressure on exhalation by for example 2–4 cm H2O and maintaining the original pressure on inhalation. Alternatively, the processor can trigger the addition of higher pressure on inspiration, for example 2 cm H2O, above the original continuous pressure level and then titration of the inspiratory pressure and or expiratory pressure until the cluster is aborted. According to the present invention, if pathophysiologic divergence is identified with a fall in oxygen saturation in relation to a rise in ventilation (as discussed in detail in the aforementioned co-pending application) this recognition can be used to automatically warn of the potential need for oxygen or to automatically initiate or increase oxygen instead of increasing the CPAP or Ventilation. Also the development of pathophysiologic divergence in association with upward titration can be used to reduce the pressure to their original levels. Automatic conversion to ventilation or increasing ventilation upon the occurrence of polymorphic clusters and/or when the cluster peaks exhibit a significant decline or automatically aborting the titration and/or providing an output indication that the patterns indicate that attended titration may be preferable provides a more physiologically focused titration of therapy which can substantially improve the efficacy and sale of automatic positive pressure treatment devices.

According to the present invention, a wide range of variations of events, reciprocations and clusters are built from simpler objects and this provides the ability to identify a wide range of physiologic phenomena without losing information gained by aggregating specific types of such phenomena. For this reason the presently preferred time domain analysis starts with a basic segmentation process upon which is built a more complex characterization. The more complex physiologic occurrences are better represented programmatically than mathematically and this representation follows. Because the wide range of permutations causes marked complexity, the present inventors recognized that an effective framework and methodology was required to address the complexity of this type of software system. In the presently preferred embodiment object oriented time series segmentation, in the time domain, into an inheritance based relational hierarchy allows recognition and characterization a very broad range of real-world phenomena including complex, interactive physiological datasets.

Figure 11:
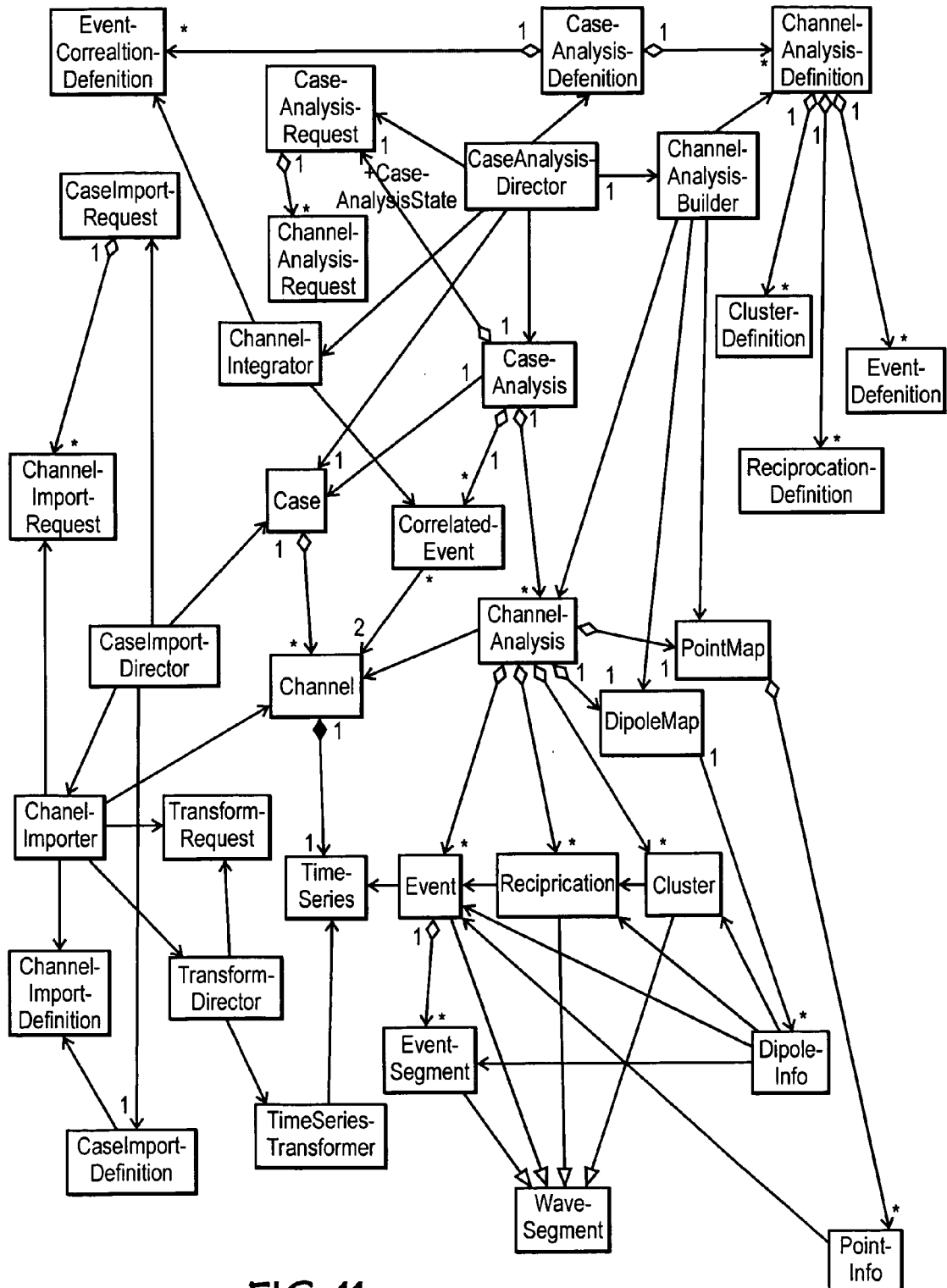
FIG. 11 show a diagram represents both the real-world objects (e.g. reciprocations) and support objects for the rapid creation, rendering of such object to a graphical user interface and persisting such objects to relational database and/or a hierarchical data store (e.g. eXtensible Markup Language (XML) documents).

The diagram of FIG. 11 represents both the real-world objects (e.g. reciprocations) and support objects for the rapid creation, rendering of such object to a graphical user interface and persisting such objects to relational database and/or a hierarchical data store (e.g. eXtensible Markup Language (XML) documents). This diagram is only representative and objects for accomplishing such rendering and persisting are not shown and may according to the present invention vary greatly depending upon the operating environment of the application.

Figure 12:
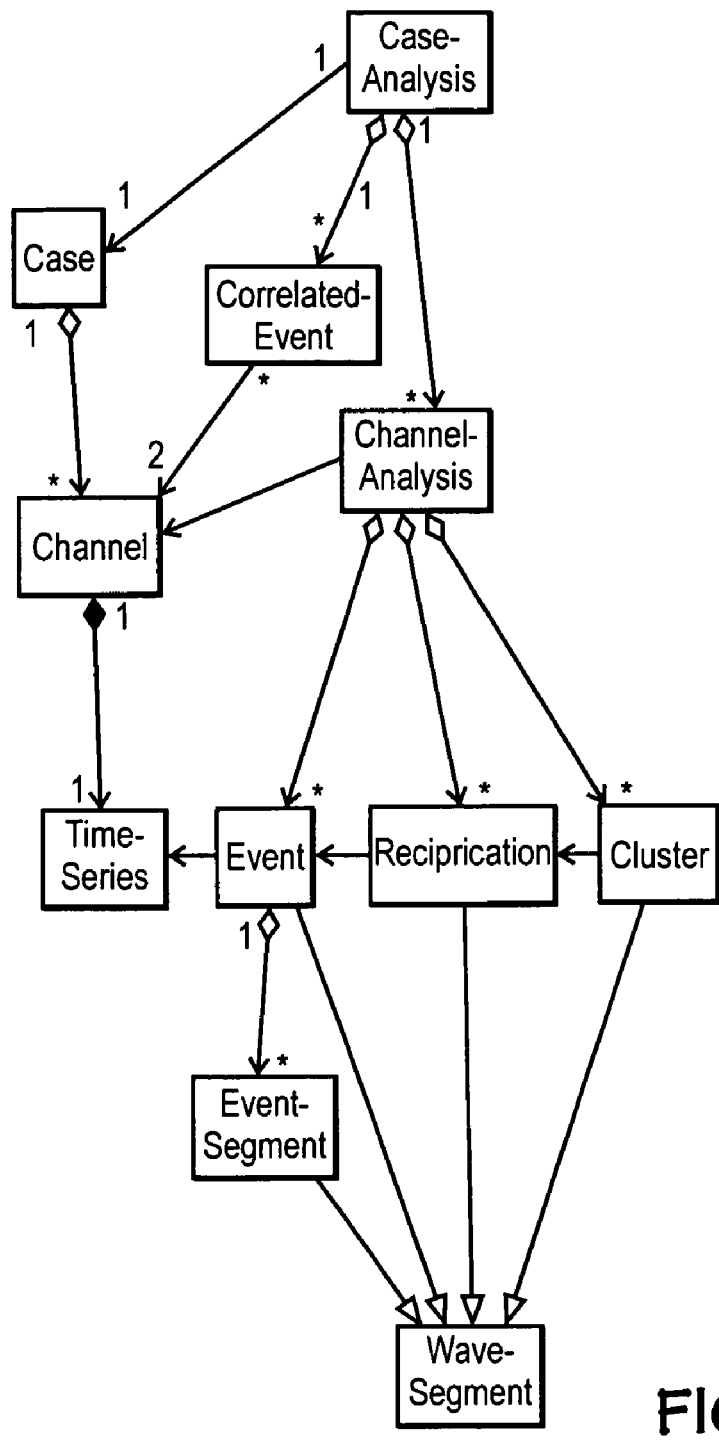
FIG. 12 shows core objects of the presently preferred analysis.

The core objects of the presently preferred analysis are shown in FIG. 12. Here a case represents a single timed data set (such as 12 or 24 hours holter monitoring period, one night in the sleep lab or hospital, or a variable post operative period) outputted from the monitored patient and may contain any number of channels. A channel is a single data stream (e.g. oximetry). A time series (as described earlier) is a set of contiguous data points derived from a particular physiologic signal (e.g. oximetry). As shown, a case is any number of channels and a channel contains a single time series. These raw data datasets are then converted (as described earlier) into objects of increasing complexity-events, reciprocations and clusters (of events and/or reciprocations). Each of these objects are representations of a segment of the wave (as designated by their reference to the WaveSegment object) but contain much more information than simply the raw data as provided by their context within the analysis (their relationship to other objects). It should be noted that the relationship to predecessor objects is maintained to provide for the layered complexity as described earlier.

Since the creation of hundreds of thousands of dipole objects can hamper the acquisition of the analysis in a real-time environment, in the presently preferred embodiment, the logical concept of the dipole object has been encapsulated within the time series to improve performance in a real time environment.

Correlated events provide the basic mechanism for identifying relationship between channels. The aggregation of these objects within a case analysis object provides the ability to interpret broad, intra and inter-channel trends while also providing access to the large amount of simple objects and raw data from which those trends were derived.

according to the present invention this presently preferred structure in the context of an object-oriented programming language that provides the power to readily apply a broad range of expert system based comparisons, create indices, alarms, graphical representations and other human facing mechanisms for interpretation and analysis. FIG. 12 shows the basic relationships of the objects created. In a completed analysis potentially thousands of such objects are created and related to each other. Further, within each object a wide range of rich functionality is exposed. As an example, the time series object exposes the following functions:

TimeSeriesKey
SampleRate
UpperLimit
LowerLimit
NumberOfPoints
StartTime
CreateTime
StartPointPosition
EndPointPosition
Duration
EndTime
MeanValue
MaxValue
MimValue
ValueAtPoint
SumAtPoint
StartSequentialLoad
SequentialLoadPoint
TimeAtPoint
DipolesToTimeSpan
TimeSpanToDipoles
TimeToNearestPoint
CompareTime
ComparePointPosition
DipolePointPosition1
DipolePointPosition2
DipoleDuration
NumberOfDlipoles
DipoleChange
DipoleSlope
DipolePolarity
MeanValueOfSegment
MinValueOfSegment
MaxValueOfSegment
DipolePositionAfter
ExtractKey
PointsNeedToBeSaved As a further example, the following is a list of functions available for a cluster object (this does not include the ability of that object to access any functionality of the reciprocations, events and time series which are related to the cluster object):

NumberOfPoints
NumberOfDipoles
StartPointPosition
EndPointPosition
StartDipolePosition
EndDipolePosition
StartTime
Duration
EndTime
MinValue
MaxValue
MeanValue
ChangeAccordingToEndPoints
SlopeAccordingToEndPoints
CompareTime
ComparePointPosition
ClusterType
ClusteredReciprocations
MeanStartEventDuration
MeanEndEventDuration
MeanStartEventMagnitude
MeanEndEventMagnitude
MeanStartEventSlope
MeanEndEventSlope
MeanReciprocationMaxValue
MeanReciprocationMinValue
MeanReciprocationMagnitude
MeanReciprocationDurationRatio
MeanReciprocationMagnitudeRatio
MeanReciprocationSlopeRatio
MeanRecoveryDuration
MeanRecoveryRatio( )

Figure 13:
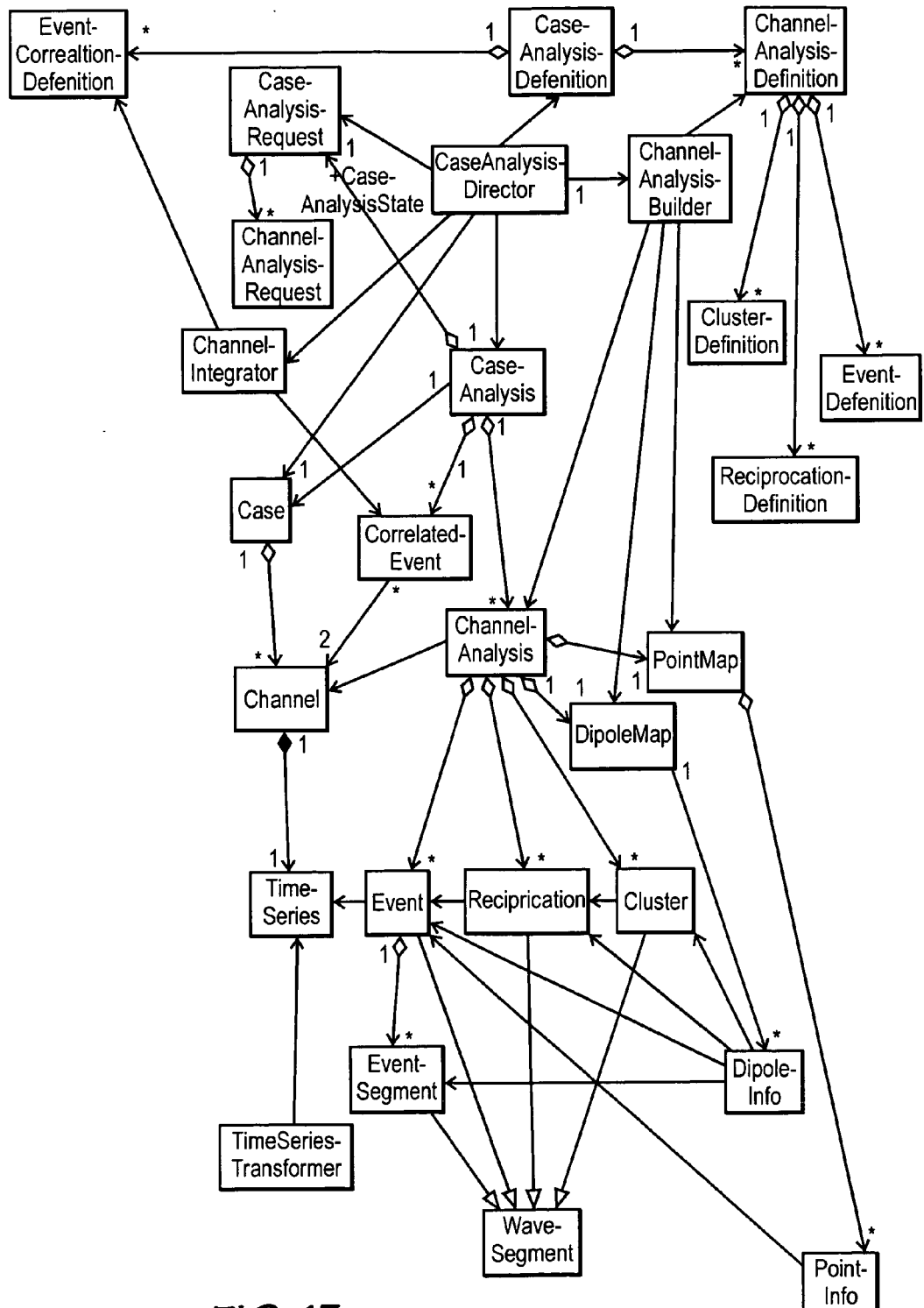
FIG. 13 shows the preferred support mechanisms for the creation of the analysis.

FIG. 13 shows the preferred support mechanisms for the creation of the analysis. In the presently preferred embodiment the analysis definition is separated from the analysis itself allowing for the efficient proliferation of patient data and analysis while maintaining a small set of metadata. Although the analysis and transforms may be fixed for application in the hospital, this flexibility allows researchers the ability to create any number of analysis definitions to apply to various patient types, and/or disorders.

As shown, in the above structure a requesting system will create an analysis request and submit it to the case analysis director. The director is a dispatcher object that oversees the analysis process while delegating the actual processing to other objects. The most important of these delegates is the channel analysis builder. This object performs the basic algorithms described above against the respective time series to produce the aforementioned events, reciprocations, clusters and the relationships between them.

During this process data structures for providing fast access by point and dipole are created as point and dipole maps respectively. These objects provide single step access to all objects tied to a particular point and/or dipole. This supports a high level of interactivity (e.g. mouse over actions) in a graphic user interface (e.g. a Microsoft Windows application).

Analysis requests may not be comprehensive and therefore further analysis can be requested to the case analysis director. This ability to provide partial analysis further enhances performance by allowing a researcher or physician to specify the particular aspects of the analysis he/she finds useful.

The channel integrator performs intra-channel analysis to create event correlations. These correlations (and the aggregations thereof) provide an integrated view of all channels within a case.

Figure 14:
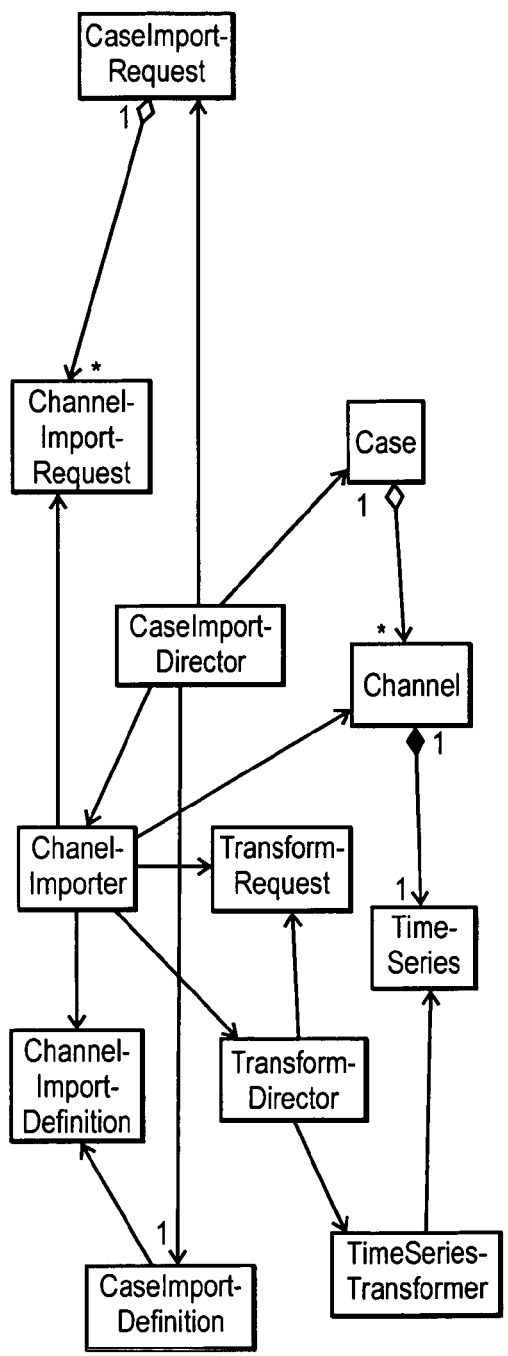
FIG. 14 shows one preferred data acquisition and transformation system for preceding the analysis.

FIG. 14 shows one preferred data acquisition and transformation system for preceding the analysis. The time series acquisition and transformation system of FIG. 14 provides for a flexible interface (real-time and otherwise) to data providers and data stores. The import and transform subsystems follow a similar design pattern of a request, a director and a set of delegate objects to perform the required operations. The present embodiment allows researchers the ability to readily transform (e.g. filter, smooth, integrate) the time series before performing analysis. The results of these transformations can then become a channel within the case itself on which analysis can be performed in the same aforementioned way. These channels can be, for example, a real-time time series of a calculated index of two or more signals such as airflow and oximetry to quickly identify pathophysiologic divergence of these normally linked parameters in postoperative patients or those at risk for pulmonary embolism or sepsis. In another example the new channel can be a real-time integration of oximetry and pulse to improve automatic severity indexing during monitoring for neonatal apnea)

Of course, the transformation itself can be a quite complex process and the transform has a substantial impact on the waveform morphology and relationships. This has been a significant problem with standard hospital monitoring systems (such as pulse oximeters). Despite the importance of the effect a transform has on time series morphology and alarm reliability the monitoring industry has not standardized to any transform and many oximeters do not even provide documentation relevant the transform applied to generate the time series. The present inventors recognized that, in the interest of providing optimal patient care, the transform needs to be understood by the physician and researcher so that the time series outputs and all algorithms performed are clearly identified and/or can be explicitly requested. For this purpose, the present inventors created a nomenclature for explicit representation of all transformations available.

FIG. 17 shows one presently preferred nomenclature for the exemplary parameters of airflow, pulse, and oxygen saturation. Illustrative examples of designation by this nomenclature are shown in FIG. 18.

According to the present invention, objects at the composite level encapsulate the objects from which they are derived at the fundamental level. For this reason a recovery object recognized at the composite level in one parameter can used to specify a region for comparison of sequential objects (such as reciprocations) at the fundamental object level in the same parameter or in matched recovery objects along another parameter. For example, upon recognition of the presence of a recovery object (where it is anticipated that the ventilation effort will be high) the ratio of the slope of fall (exhalation) objects and rise (inhalation) objects at the fundamental level can be compared within the recovery object and the time series derived from an continuous calculation this ratio can be plotted at it too analyzed by object mapping if desired. During upper airway obstruction, the inspiration is slowed to a greater degree than exhalation. The magnitude change of inspiratory slowing and/or amplitude and/or ratio during the clusters of apneas provides an index of the magnitude of upper airway narrowing (which slows inhalation during the clustered apnea/hypopnea objects). However, during the recovery object or at the "hyperventilation reference point", the upper airway should be wide open for both inhalation and exhalation and this can be used as a reference because, during this time,. Because the recovery objects encapsulate the fundamental reciprocation objects from which it is derived, the absolute slope, magnitude, frequency and amplitude, of the fundamental objects during recovery can then be compared to provide a reference for the absolute slope magnitude, frequency and amplitude of the fundamental objects during other times along the night to provide an indication of upper or lower airway narrowing.

These encapsulations allow ready exploitation that certain regions along a multi-signal object (as within an airway instability cluster) have a very high probability of association with various levels of ventilation. According to the present invention, the objects defining those regions can then be used as a reference or as an opportunity to examine for the effects of a given level of ventilation effort on the flow characteristics of the encapsulated reciprocations. Patients with obstructive sleep apnea are expected to have a fall in the slopes of fundamental inspiration objects during decline objects at the composite level indicative of upper airway narrowing and/or occlusion. Also, as shown in FIG. 7, patients with asthma or chronic obstructive lung disease may have a reduced slope of the exhalation when compared to the slope of inhalation during the rise objects between apneas at the base level. According one embodiment of the present invention, the ratio of the slope of inhalation objects at the fundamental level is compared to the slope of the exhalation objects at the fundamental level and this can be plotted as a time series for object based analysis. Patients with simple, uncomplicated obstructive apnea will have clusters of increasing slope ratios with the ratio rising to about one during the recovery objects. Patients with combined obstructive apnea and asthma or chronic obstructive lung disease will have increased ratios during the recovery objects into the range of 2–3 or greater, indicating the development of obstructive lower airways during the rapid breathing associated with recovery.

Another example of object processing at the fundamental object level, according to the present invention, includes the processor-based identification of fluttering of the plateau on the pressure signal to recognize partial upper airway obstruction. During the nasal pressure monitoring a fluttering plateau associated with obstructive breathing often occurs intervening a rise event and a fall event of tidal breathing. Since the plateau objects are easily recognizable at the fundamental level and readily separated using the present object recognition system the plateau can be processed for the tiny rise and fall objects associated with fluttering and the frequency of these objects can be determined. Alternatively, a Fourier transform can be applied to the plateau objects between the rise and fall events of the nasal pressure signal to recognize the presence of fluttering or another method can be utilized which provides an index of the degree of fluttering of the plateau objects.

Since reduced effort also lowers the slope of exhalation and inspiration, the configuration (as defined by the slope dataset of the dipoles defining the fundamental objects of both inspiration and expiration at the reference objects) can be applied as reference fundamental object configurations defining the presence of hyperventilation or hypopnea. This process is similar to the selection process for identifying search objects described earlier but in this case the input region is pre-selected. In an example, the range of characteristics of the objects at the fundamental level derived from one or more tidal breaths occurring prior to the second airflow delta point can be used to designate a reference hyperventilation objects range. Alternatively the object based characteristics, defined by of the range of characteristics of the objects derived from one or more tidal breaths occurring prior to the first airflow delta point can be used designate a reference hypopnea objects range. The processor can then automatically assess object ranges along other points of the tracing. In this way the processor can apply an artificial intelligence process to the identification of hypopneas by the following process:

1. Identify the region wherein a hypopnea is expected (as for example two to three tidal breaths prior to the first airflow delta point).
2. Select this as a region for objects processing to define the characteristics of hypopneas in this patient.
3. Process the region using the slope dipole method to define the range of fundamental objects comprising the target region.
4. Compare the identified range of objects to other analogous objects along to tracing to identify new objects having similar characteristics.
5. Using the criteria derived from the objects defining the target region search the processed waveform for other regions having matching sequences of new objects and identifies those regions.
6. Provide an output based on said identification and/or take action (e.g. increase CPAP) based on said identification.

In one embodiment, the multi-signal time series output is placed into a format particularly useful for demonstrating events to hospital personal especially for teaching purposes. In this format the output controls an animation of multiple objects which are shaped into an animated schematic of the as the physiologic system being monitored. The animation moves over time and in response to the signals and one preferred embodiment the type of signals (or the reliability of such signals) determines which components of the schematic are "turned on" and visible. One example includes a multi-signal object defined by outputs of airflow, thoracic impedance, oximetry, and blood pressure rendering set of a connected set animation objects for the lungs, upper airway, lower airway, heart, and blood vessels which can be animated as;

Each inspiration causing an animated enlargement of the lungs tracking the inspiration slope,
Each expiration causing an animated reduction in size of the lungs tracking the expiration slope,
Each animated systolic beat of the heart tracks the QRS or upstroke of the oximetry output,
The color of the blood in the arteries and left heart tracks the oxygen saturation,
The diameter of the lower airway (a narrowing diameter can be highlighted in red) tracks the determination of obstruction by the slope ratio in situations of hyperventilation (as discussed previously),
The patency of the upper airway (a narrowing or closure can be highlighted in red) tracks the determination of upper airway obstruction (for example the airway is shown as opening and closing in clusters when ventilation effort (as by chest wall movement) is identified in clusters with absent nasal flow.

This provides "physiologic animation" which can be monitored in real-time and which can also be derived and reviewed from the stored multi-signal objects at variable time scales. This embodiment of the present invention provides a quickly, easily understood and dynamic animated output of a highly complex, interactive time series derived from a patient. The animation can be reviewed at an increased time lapsed to speed through evolution of a given patients outputs or can be slowed or stopped to see the actual global physiologic state at the point of onset or termination of a given pathophysiologic perturbation.

Figure 19:
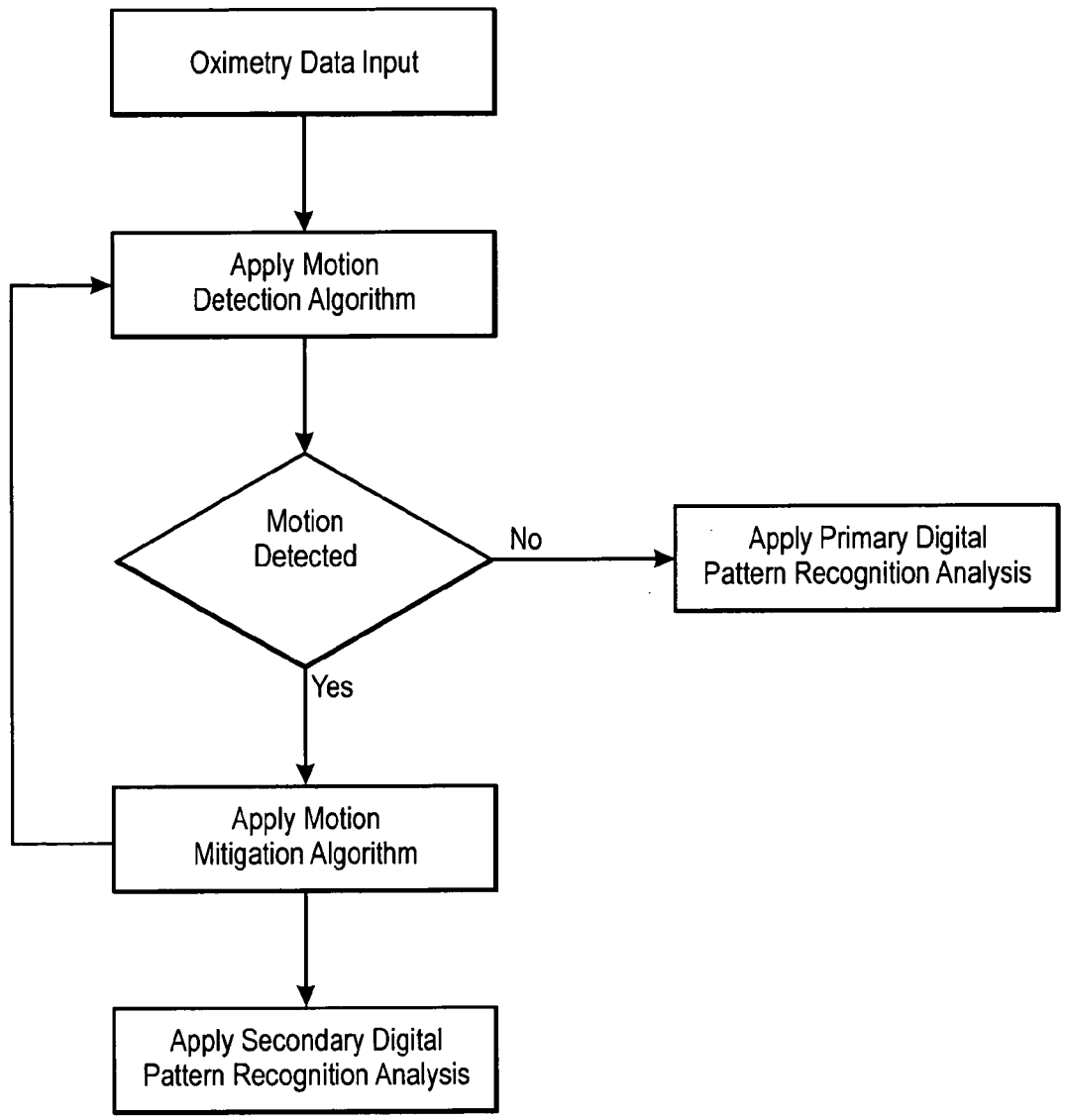
FIG. 19 shows a schematic of a system for automatically changing the processing analysis of subsequent time-series portion based on the analysis output of an earlier portion of the time series

Particularly for use in the hospital, a graded indicator or alarm can be provided, indicative of the severity of the clusters and of airway or ventilation instability. Since very mild clustering may simply represent the effect of moderate sedation, and not, therefore, represent a cause for great concern (although it is important to recognize that it is present). Such a clustering could be identified with a single bar or test warning, whereas more severe clustering would generate a larger warning and, if very severe, an auditory alarm. When the clustering becomes more severe and demonstrates greater levels of desaturation and/or shorter recovery intervals the bar can be doubled According to another aspect of the present invention, a change in one or more time series components of the multi-signal object can be used to change the processing algorithm of a time series component of the multi-signal object. In an example, the recognition of airway instability is enhanced by improved fidelity of the timed waveform (as with pulse oximetry). FIG. 19 shows one preferred method, according to the present invention, of improving the general fidelity of the entire timed waveform of $SpO_2$ for enhanced pattern & cluster recognition in an environment where the patient, at times, has motion and, at other times, does not. It is optimal, for example, in monitoring oximetry for the probe to be placed on a portion of the patient, which is not associated with motion. However, in most cases, this is unrealistic and motion is commonly associated with routine clinical oximetry monitoring. It is well known that motion results in a fall in the saturation value, which is generated by the oximeter. Multiple theories for the cause of the fall have been promulgated. Several corporations, including Masimo, and Nellcor had developed algorithms, which can be used to mitigate the effect of motion on the accuracy of the output. However, such algorithms can include a significant amount of signal averaging, generally four seconds or more. This can result in significant smoothing of the waveform and reduces the fidelity of the waveform. Furthermore, it attenuates patterns of minor desaturations, which can be indicative of airway instability, and clusters of hypopneas associated with variations in airway resistance. As discussed in the aforementioned patents and patent application, even minor desaturations when occurring in clusters can be strong evidence for airway or ventilation instability and it is important to recognize such desaturations. Unfortunately, averaging intervals, especially those exceeding four seconds or more can result in attenuation of these desaturations and, therefore, hide these clusters so that the airway instability may not be recognized. However, motion itself results in artifact, which can simulate desaturations. Although such artifact is not expected to occur in typical cluster pattern, the presence of motion artifacts significantly reduces the value of the signal as an index of oxygen saturation and airway instability.

The present invention thereby provides for more optimal continuous fidelity of the waveform through both motion and non-motion states. As illustrated in FIG. 16, when the motion time series output suggests that substantial motion is not present, such as deep sleep or sedation, wherein the extremity is not moving, long averaging smoothing algorithms or motion mitigation algorithms are not applied to the oxygen saturation and plethesmographic pulse time series. In the alternative, if the series indicates motion then these motion mitigation algorithms are applied. The variable application of averaging based on identification of the absence or presence of motion provides optimal fidelity of the waveform for monitoring airway instability.

Those skilled in the art will recognize that, the information provided from the data and analysis generated from the above-described system can form the basis for other hardware and/or software systems and has wide potential utility. Devices and/or software can provide input to or act as a consumer of the physiologic signal processing system of the present invention's data and analysis.

The following are examples of presently preferred ways that the present physiologic signal processing system can interact with other hardware or software systems:
1. Software systems can produce data in the form of a waveform that can be consumed by the physiologic signal processing system.
2. Embedded systems in hardware devices can produce a real-time stream of data to be consumed by the physiologic signal processing system.
3. Software systems can access the physiologic signal processing system representations of populations of patients for statistical analysis.
4. Software systems can access the physiologic signal processing system for conditions requiring hardware responses (e.g. increased pressure in a CPAP device), signal the necessary adjustment and then analyze the resulting physiological response through continuous reading of the physiologic signal processing system data and analysis.

It is anticipated that the physiologic signal processing system will be used in these and many other ways. To facilitate this anticipated extension through related hardware and software systems the present system will provide an application program interface (API). This API can be provided through extendable source code objects, programmable components and/or a set of services. Access can be tightly coupled through software language mechanisms (e.g. a set of C++ modules or Java classes) or proprietary operating system protocols (e.g. Microsoft's DCOM, OMG's CORBA or the Sun Java Platform) or can be loosely coupled through industry standard non-proprietary protocols that provide real-time discovery and invocation (e.g. SOAP [Simple Object Access Protocol] or WSDL [Web Service Definition Language]).

In the preferred embodiment the physiologic signal processing system with the API as defined becomes a set of programmable objects providing a feature-rich development and operating environment for future software creation and hardware integration.

The program is particularly suited for physiologic signals but can be used to track and identify relationships between a broad range of signals to identify specific patterns or to search for patterns. Although the listed program is coded for contiguous points for efficiency, according to the present invention, the time series data points need not be contiguous and indeed as discussed with physiologic data sets, noncontiguous points are converted into a time series when nadirs or peaks of reciprocations are plotted to identify timed patterns of variation in these parameters. The present invention is applicable to detect dynamic patterns and relationships particularly in the time domain in the along and between one or a plurality of financial time series such as stock prices or stock indexes, vibration time series, time series of sound, air movement, temperature, populations, and other dynamic processes where it may be desirable to identify, along complex data sets, known or unknown dynamic patterns of interaction.

Although the presently preferred embodiments have been described, which relate to the processing of physiologic signals, it is also critical to recognize the present streaming parallel objects based data organization and processing method can be used to order and analyze a wide range of dynamic patterns of interactions across a wide range of corresponding signals and data sets in many environments. The invention is especially applicable to the monitoring of the variations or changes to a physical system, biologic system, or machine subjected to a specific process or group of processes over a specific time interval.

Many other additional parameters may be added and will become evident to those skilled in the art in association with the application of the present invention and these are included within the scope of this invention. Those skilled in the art that various changes and modifications can be made without departing from the invention. While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method for the automatic detection of obstructive sleep apnea in a centralized hospital critical care monitoring system for the monitoring by telemetry of a plurality of patients in at least one of a critical care ward and a hospital ward, the system including a central processor having a display, and a plurality of telemetry units for mounting with said patients, each of said telemetry units having a plurality of sensors for connection with each said patient, each of said telemetry units transmitting a plurality of signals to said central processor, the method comprising the steps of:
   a) programming said system to analyze said signals and to-automatically identify at least one of the presence and severity of obstructive sleep apnea,
   b) programming said system to output an indication of said identified obstructive sleep apnea; and
   c) programming said system to communicate with an intravenous infusion system to prevent the progression of said identified obstructive sleep apnea by limiting infusion of a narcotic.

2. A method for providing automatic detection of upper airway instability in hospitalized patients who are being otherwise routinely monitored with a centralized hospital monitoring system, in at least one of an acute care environment or a surgical hospital environment, so that the routine monitoring provides automatic screening for upper airway instability, the method comprising the steps of:
   a) programming said centralized system to automatically identify the presence of upper airway instability;
   b) programming said centralized system to output an indication of said identified upper airway instability; and
   c) programming said centralized system to communicate with an intravenous infusion system to prevent the progression of said identified upper airway instability by limiting infusion of a narcotic.

3. The method of claim 2, further comprising the steps of:
a) programming said centralized system to automatically identify the presence of obstructive sleep apnea; and
b) outputting an indication of said identified obstructive sleep apnea.

4. The method of claim 2, wherein said method further comprises the step of:
programming said centralized system to provide a graded indication based on said identified upper airway instability.

5. The method of claim 2, wherein said method further comprises the step of:
programming said centralized system to communicate with a system for intravenously infusing a medication.

6. The method of claim 2, wherein said method further comprises the step of:
programming said centralized system to communicate with an airway pressure delivery system for treatment of airway instability.

7. A method for facilitating case finding of obstructive sleep apnea in hospitalized patients who are being otherwise routinely monitored with a centralized hospital monitoring system in at least one of an acute care environment, a sub acute care environment and a surgical hospital environment, the method comprising:
a) programming said centralized system to provide a printed output that is formatted to optimize the visual detection of patterns indicative of the presence of obstructive sleep apnea disease, so that routine hospital monitoring renders printed outputs that can be readily interpreted to routinely detect the presence of obstructive sleep apnea disease; and
b) programming said centralized system to communicate with an intravenous infusion system to reduce the progression of an identified upper airway instability by limiting the infusion of a narcotic.

* * * * *